(12) United States Patent
Harding

(10) Patent No.: US 7,773,724 B2
(45) Date of Patent: Aug. 10, 2010

(54) SYSTEMS AND METHODS FOR GENERATING AN IMPROVED DIFFRACTION PROFILE

(75) Inventor: Geoffrey Harding, Hamburg (DE)

(73) Assignee: Morpho Detection, Inc., Newark, CA (US)

( * ) Notice: Subject to any disclaimer, the term of this patent is extended or adjusted under 35 U.S.C. 154(b) by 254 days.

(21) Appl. No.: 11/484,533

(22) Filed: Jul. 11, 2006

(65) Prior Publication Data

US 2008/0013684 A1   Jan. 17, 2008

(51) Int. Cl.
*G01N 23/201*   (2006.01)
*G01N 23/207*   (2006.01)

(52) U.S. Cl. .......................................... 378/86; 378/71

(58) Field of Classification Search .................... 378/57, 378/86, 88, 90, 70, 71, 82, 83
See application file for complete search history.

(56) References Cited

U.S. PATENT DOCUMENTS

| | | | |
|---|---|---|---|
| 4,672,648 A | | 6/1987 | Mattson et al. |
| 5,115,459 A | * | 5/1992 | Bertozzi ...................... 378/88 |
| 6,684,676 B2 | | 2/2004 | Oumi et al. |
| 6,693,988 B2 | * | 2/2004 | Harding ........................ 378/86 |
| 7,286,638 B2 | * | 10/2007 | Ledoux et al. ................ 378/88 |
| 7,365,536 B2 | | 4/2008 | Crowley et al. |
| 2004/0222790 A1 | | 11/2004 | Karmi et al. |
| 2005/0094767 A1 | * | 5/2005 | Francke et al. ................ 378/87 |
| 2005/0281383 A1 | | 12/2005 | Harding et al. |
| 2006/0140340 A1 | * | 6/2006 | Kravis .......................... 378/57 |

FOREIGN PATENT DOCUMENTS

WO   WO 2004105610 A1 * 12/2004

OTHER PUBLICATIONS

Quantum Magnetics, i-Portal, 2001, web archive, Business Wire, Nov. 1, 2001, p. 1-2.
International Search Report, PCT/US2007/072744, dated Mar. 20, 2009, p. 3.

* cited by examiner

*Primary Examiner*—Edward J Glick
*Assistant Examiner*—Anastasia Midkiff
(74) *Attorney, Agent, or Firm*—Armstrong Teasdale LLP

(57) ABSTRACT

A system for generating an improved diffraction profile is described. The system includes at least one x-ray source configured to generate x-rays and a primary collimator outputting a first x-ray beam to a first focus point and a second x-ray beam to a second focus point. The primary collimator generates the first and second x-ray beams from the x-rays. The system further includes a container, and a first scatter detector configured to detect a first set of scattered radiation generated upon intersection of the first x-ray beam with the container and to detect a second set of scattered radiation generated upon intersection of the second x-ray beam with the container. An angle of scatter of the first set of scattered radiation detected by the first scatter detector is at most half of an angle of scatter of the second set of scattered radiation detected by the first scatter detector.

20 Claims, 12 Drawing Sheets

SYSTEMS AND METHODS FOR GENERATING AN IMPROVED DIFFRACTION PROFILE

BACKGROUND OF THE INVENTION

This invention relates generally to systems and methods for generating a diffraction profile and more particularly to systems and methods for generating an improved diffraction profile.

The events of Sep. 11, 2001 instigated an urgency for more effective and stringent screening of airport baggage. The urgency for security expanded from an inspection of carry-on bags for knives and guns to a complete inspection of checked bags for a range of hazards with particular emphasis upon concealed explosives. X-ray imaging is a widespread technology currently employed for screening. However, existing x-ray baggage scanners, including computed tomography (CT) systems, designed for detection of explosive and illegal substances are unable to discriminate between harmless materials in certain ranges of density and threat materials like plastic explosive.

A plurality of identification systems based on a plurality of x-ray diffraction (XRD) techniques provide an improved discrimination of materials compared to that provided by the x-ray baggage scanners. The XRD identification systems measure a plurality of d-spacings between a plurality of lattice planes of micro-crystals in materials.

However, the XRD identification systems are inefficient because the XRD identification systems consume a high amount of power. Moreover, it is difficult for the XRD identification systems to examine a large suitcase.

BRIEF DESCRIPTION OF THE INVENTION

In one aspect, a system for generating an improved diffraction profile is described. The system includes at least one x-ray source configured to generate x-rays and a primary collimator outputting a first x-ray beam to a first focus point and a second x-ray beam to a second focus point. The primary collimator generates the first and second x-ray beams from the x-rays. The system further includes a container, a first scatter detector configured to detect a first set of scattered radiation generated upon intersection of the first x-ray beam with the container and to detect a second set of scattered radiation generated upon intersection of the second x-ray beam with the container. An angle of scatter of the first set of scattered radiation detected by the first scatter detector is at most half of an angle of scatter of the second set of scattered radiation detected by the first scatter detector.

In another aspect, a system for generating an improved diffraction profile is described. The system includes at least one x-ray source configured to generate x-rays and a primary collimator outputting a first x-ray beam to a first focus point and a second x-ray beam to a second focus point. The primary collimator generates the first and second x-ray beams from the x-rays. The system further includes a container, and a first scatter detector configured to detect a first set of scattered radiation generated upon intersection of the first x-ray beam with the container and to detect a second set of scattered radiation generated upon intersection of the second x-ray beam with the container. An angle of scatter of the first set of scattered radiation detected by the first scatter detector is at most half of an angle of scatter of the second set of scattered radiation detected by the first scatter detector. The system also includes a processor coupled to the first scatter detector and configured to generate a portion of a diffraction profile from the first and second sets of scattered radiation detected by the first scatter detector.

In yet another aspect, a method for generating an improved diffraction profile is described. The method includes generating x-rays by activating at least one x-ray source and outputting, by a primary collimator, a first x-ray beam to a first focus point and a second x-ray beam to a second focus point. The primary collimator generates the first and second x-ray beams from the x-rays. The method further includes detecting, by a first scatter detector, a first set of scattered radiation generated upon intersection of the first x-ray beam with a container and detecting, by the first scatter detector, a second set of scattered radiation generated upon intersection of the second x-ray beam with the container. An angle of scatter of the first set of scattered radiation detected by the first scatter detector is at most half of an angle of scatter of the second set of scattered radiation detected by the first scatter detector.

DETAILED DESCRIPTION OF THE INVENTION

Figure 1:
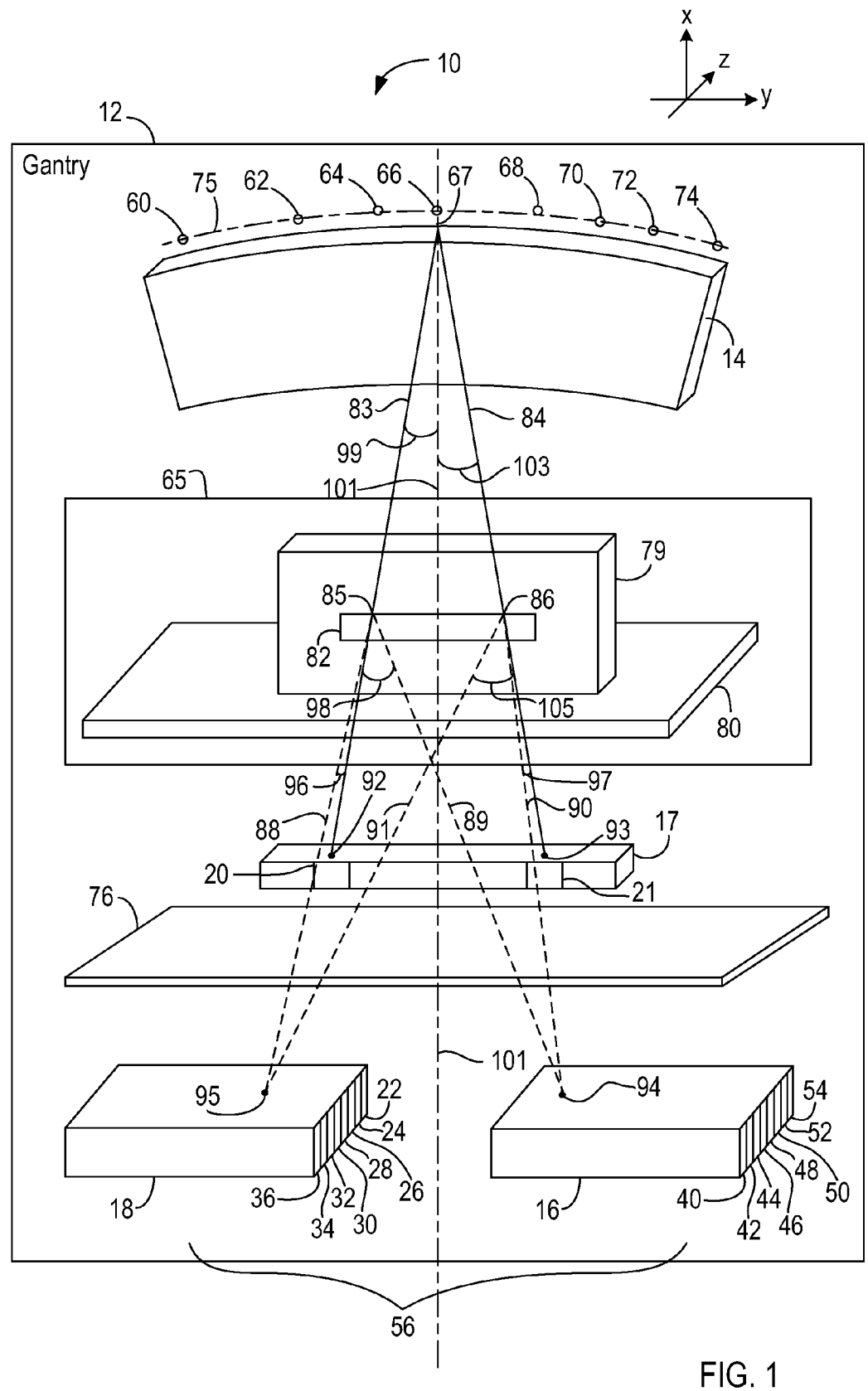
FIG. 1 is an isometric view of an embodiment of a system for generating an improved diffraction profile of a substance.

FIG. 1 is an isometric view of an embodiment of a system 10 for generating an improved diffraction profile of a substance. System 10 includes a gantry 12. Gantry 12 includes a primary collimator 14, a scatter detector 16, a transmission detector 17, a scatter detector 18, and a secondary collimator 76. Each scatter detector 16 and 18 is a segmented semiconductor detector.

Transmission detector 17 includes a plurality of detector elements, such as detector elements 20 and 21. Scatter detector 18 includes a plurality of detector cells or detector elements 22, 24, 26, 28, 30, 32, 34, and 36 for detecting coherent scatter. Scatter detector 16 includes a plurality of detector cells or detector elements 40, 42, 44, 46, 48, 50, 52, and 54 for detecting coherent scatter. Each of scatter detectors 16 and 18 include any number, such as, ranging from and including 5 to 1200, of detector elements. For example, scatter detector 18 includes a number, such as ranging from and including 5 to 40, of detector elements in a z-direction parallel to a z-axis, and a number, such as ranging from and including 1 to 30 detector elements in a y-direction parallel to a y-axis. An x-axis, the y-axis, and the z-axis are located within an xyz co-ordinate system. The x-axis is perpendicular to the y-axis and the z-axis, and the y-axis is perpendicular to the z-axis, and the x-axis is parallel to an x-direction. X-ray sources, of system 10, including x-ray sources 60, 62, 64, 66, 68, 70, 72, and 74, and transmission detector 17 form an inverse single-pass multi-focus imaging system. X-ray sources, of system 10, including x-ray sources 60, 62, 64, 66, 68, 70, 72, and 74, have an inverse fan-beam geometry that includes a symmetric location of the x-ray sources relative to the z-axis. A number of detector elements within scatter detector 16 is the same as a number of detector elements within scatter detector 18.

Scatter detector 16 is separate from scatter detector 18. For example, scatter detector 16 has a housing that is separate from a housing of scatter detector 18. As another example scatter detectors 16 and 18 are separated from each other by a gap. As yet another example, a shortest distance 56 between a center of scatter detector 16 and a center of scatter detector 18 ranges from and including 40 millimeters (mm) to 200 mm. Each of scatter detector 16, scatter detector 18, and transmission detector 17 are located in the same yz plane. The yz plane is formed by the y-axis and the z-axis. Each of scatter detector 16 and scatter detector 18 is separate from transmission detector 17 by a shortest distance ranging from and including 30 mm to 60 mm in the z-direction.

Gantry 12 further includes a plurality of x-ray sources 60, 62, 64, 66, 68, 70, 72, and 74. X-ray sources 60, 62, 64, 66, 68, 70, 72, and 74 are located parallel to and coincident with an arc 75. It is noted that in an alternative embodiment, system 10 includes a higher number, such as 10 or 20, or alternatively a lower number, such as 4 or 6, of x-ray sources than that shown in FIG. 1. A center of transmission detector 17 is located at a center of circle having arc 75. Each x-ray source 60, 62, 64, 66, 68, 70, 72, and 74 is an x-ray source that includes a cathode and an anode. Alternatively, each x-ray source 60, 62, 64, 66, 68, 70, 72, and 74 is an x-ray source that includes a cathode and all x-ray sources 60, 62, 64, 66, 68, 70, 72, and 74 share a common anode.

A container 79 is placed on a support 80 between x-ray sources 60, 62, 64, 66, 68, 70, 72, and 74 and scatter detectors 16 and 18. Container 79 and support 80 are located within an opening 65 of gantry 12. Examples of container 79 include a bag, a box, and an air cargo container 79. Examples of each x-ray source 60, 62, 64, 66, 68, 70, 72, and 74 include a polychromatic x-ray source. Container 79 includes a substance 82. Examples of substance 82 include an organic explosive, an amorphous substance having a crystallinity of less than twenty five percent, a quasi-amorphous substance having a crystallinity at least equal to twenty-five percent and less than fifty percent, and a partially crystalline substance having a crystallinity at least equal to fifty percent and less than one-hundred percent. Examples of the amorphous, quasi-amorphous, and partially crystalline substances include a gel explosive, a slurry explosive, an explosive including ammonium nitrate, and a special nuclear material. Examples of the special nuclear material include plutonium and uranium. Examples of support 80 include a table and a conveyor belt. An example of each scatter detector 16 and 18 includes a segmented detector fabricated from Germanium.

X-ray source 66 emits an x-ray beam 67 in an energy range, which is dependent on a voltage applied by a power source to x-ray source 66. Primary collimator 14 generates two primary beams 83 and 84, such as pencil beams, upon collimating x-ray beam 67 from x-ray source 66. In an alternative embodiment, primary collimator 14 collimates x-ray beam 67 received from x-ray source 66 to generates a plurality, such as three or four, primary beams. A number of primary beams generated by primary collimator 14 is equal to or alternatively greater than a number of scatter detectors on one side of transmission detector 17 and on one side of the y-axis. Primary beams 83 and 84 pass through a plurality of points 85 and 86 on substance 82 within container 79 arranged on support 80 to generate scattered radiation 88, 89, 90, and 91. For example, primary beam 83 passes through point 85 to generate scattered radiation 88 and 89. As another example, primary beam 84 passes through point 86 to generate scattered radiation 90 and 91.

Secondary collimator 76 is located between support 80 and a set of scatter detectors 16 and 18. Secondary collimator 76 includes a number of collimator elements, such as sheets, slits, or laminations, to ensure that scattered radiation arriving at scatter detectors 16 and 18 have constant scatter angles with respect to primary beams 83 and 84 and that a position of scatter detectors 16 and 18 permits a depth in container 79 at which the scattered radiation originated to be determined. For example, the collimator elements of secondary collimator 76 are arranged parallel to a direction of scattered radiation 88 and of scattered radiation 90 to absorb scattered radiation that is not parallel to the direction of the scattered radiation 88 and of scattered radiation 90.

The number of collimator elements in secondary collimator 76 provided is equal to or alternatively greater than a number of detector elements of any one of scatter detectors 16 and 18 and the collimator elements are arranged such that scattered radiation between neighboring collimator elements is incident on one of the detector elements. The collimator elements of scatter detectors 16 and 18 are made of a radiation-absorbing material, such as, steel, copper, silver, or tungsten.

Underneath support 80, there is arranged transmission detector 17, which measures an intensity of primary beam 83 at a point 92 on transmission detector 17 and an intensity of primary beam 84 at a point 93 on transmission detector 17. Moreover, underneath support 80, there are arranged scatter detectors 16 and 18 that measure photon energies of scattered radiation received by scatter detectors 16 and 18. Each of scatter detectors 16 and 18 measures the x-ray photons within scattered radiation received by scatter detectors 16 and 18 in an energy-sensitive manner by outputting a plurality of electrical output signals linearly dependent on a plurality of energies of the x-ray photons detected from within the scattered radiation. Scatter detector 16 measures scattered radiation 90 received at a point 94 on scatter detector 16 and scatter detector 18 measures scattered radiation 88 received at a point 95 on scatter detector 18. An example of a shortest distance between points 85 and 95 includes a distance ranging from and including 900 mm to 1100 mm. An example of a distance between points 95 and 92 includes a distance ranging from and including 25 mm to 80 mm.

Scatter detectors 16 and 18 detect scattered radiation to generate a plurality of electrical output signals. Scatter detector 16 detects scattered radiation 90 generated upon intersection of primary beam 84 with point 86. Moreover, scatter detector 16 detects scattered radiation 89 generated upon intersection of primary beam 83 with point 85. Scatter detector 18 detects scattered radiation 88 generated upon intersection of primary beam 83 with point 85. Moreover, scatter detector 18 detects scattered radiation 91 generated upon intersection of primary beam 84 with point 86. A scatter angle 96 formed between primary beam 83 and scattered radiation 88 is equal to a scatter angle 97 formed between primary beam 84 and scattered radiation 90. An example of each of scatter angles 96 and 97 includes an angle ranging from and including 0.025 radians to 0.045 radians. An example of a scatter angle 98 formed between primary beam 83 and scattered radiation 89 ranges from and including 0.05 radians to 0.09 radians. Moreover, an example of a scatter angle 105 formed between primary beam 84 and scattered radiation 91 ranges from and including 0.05 radians to 0.09 radians. Scatter angle 98 is at least twice of each scatter angle 96 and 97 and scatter angle 105 is at least twice of each scatter angle 96 and 97. An angle 99 formed by primary beam 83 with respect to a center 101 between scatter detectors 16 and 18 is equal to an angle 103 formed by primary beam 84 with respect to center 101. In another alternative embodiment, system 10 includes additional scatter detectors other than scatter detectors 16 and 18. The additional scatter detectors are placed on a side of transmission detector 17 that is the same as a side of placement of scatter detectors 16 and 18. Moreover, the additional scatter detectors are the same as scatter detectors 16 and 18. For example, any one of the additional scatter detectors have the same number of detector elements as that of any of scatter detectors 16 and 18.

Figure 2:
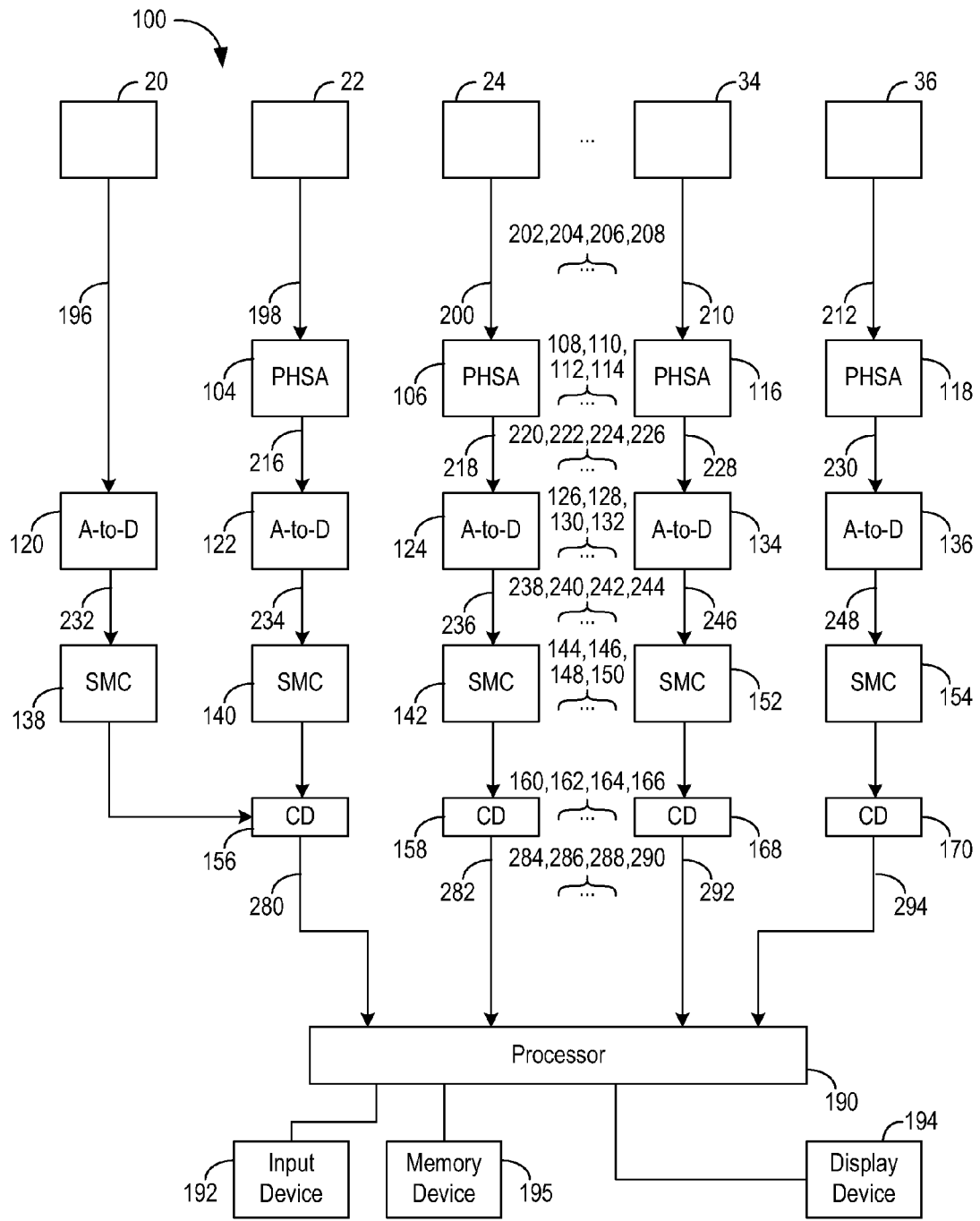
FIG. 2 is a block diagram of an embodiment of a system for generating an improved diffraction profile of a substance.

FIG. 2 is diagram of an embodiment of a system 100 for generating an improved diffraction profile of a substance. System 100 includes detector element 20 of transmission detector 17, scatter detector elements 22, 24, 26, 28, 30, 32, 34, and 36, a plurality of pulse-height shaper amplifiers (PHSA) 104, 106, 108, 110, 112, 114, 116, and 118, a plurality of analog-to-digital (A-to-D) converters 120, 122, 124, 126, 128, 130, 132, 134, and 136, a plurality of spectrum memory circuits (SMCs) 138, 140, 142, 144, 146, 148, 150, 152, and 154 allowing pulse height spectra to be acquired, a plurality of correction devices (CDs) 156, 158, 160, 162, 164, 166, 168, and 170, a processor 190, an input device 192, a display device 194, and a memory device 195. As used herein, the term processor is not limited to just those integrated circuits referred to in the art as a processor, but broadly refers to a computer, a microcontroller, a microcomputer, a programmable logic controller, an application specific integrated circuit, and any other programmable circuit. The computer may include a device, such as, a floppy disk drive or CD-ROM drive, for reading data including the methods for developing a primary collimator from a computer-readable medium, such as a floppy disk, a compact disc-read only memory (CD-ROM), a magneto-optical disk (MOD), or a digital versatile disc (DVD). In another embodiment, processor 190 executes instructions stored in firmware. Examples of display device 194 include a liquid crystal display (LCD) and a cathode ray tube (CRT). Examples of input device 192 include a mouse and a keyboard. Examples of memory device 195 include a random access memory (RAM) and a read-only memory (ROM). An example of each of correction devices 156, 158, 160, 162, 164, 166, 168, and 170 include a divider circuit. Each of spectrum memory circuits 138, 140, 142, 144, 146, 148, 150, 152, and 154 include an adder and a memory device, such as a RAM or a ROM.

Detector element 20 is coupled to analog-to-digital converter 120, and detector elements 22, 24, 26, 28, 30, 32, 34, and 36 are coupled to pulse-height shaper amplifiers 104, 106, 108, 110, 112, 114, 116, and 118, respectively. Detector element 20 generates an electrical output signal 196 by detecting primary beam 83 and detector elements 22, 24, 26, 28, 30, 32, 34, and 36 generate a plurality of electrical output signals 198, 200, 202, 204, 206, 208, 210, and 212 by detecting scattered radiation. For example, detector element 22 generates electrical output signal 198 for each scattered x-ray photon incident on detector element 22. Each pulse-height shaper amplifier amplifies an electrical output signal received from a detector element. For example, pulse-height shaper amplifier 104 amplifies electrical output signal 198 and pulse-height shaper amplifier 106 amplifies electrical output signal 200. Pulse-height shaper amplifiers 104, 106, 108, 110, 112, 114, 116, and 118 have a gain factor determined by processor 190.

An amplitude of an electrical output signal output from a detector element is proportional to an energy of an x-ray quantum that is detected by the detector element to generate the electrical output signal. For example, an amplitude of electrical output signal 196 is proportional to an energy of an x-ray quantum in primary beam 83 detected by detector element 20. As another example, an amplitude of electrical output signal 198 is proportional to an energy of an x-ray quantum within scattered radiation that is detected by detector element 22.

A pulse-height shaper amplifier generates an amplified output signal by amplifying an electrical output signal generated from a detector element. For example, pulse-height shaper amplifier 104 generates an amplified output signal 216 by amplifying electrical output signal 198 and pulse-height shaper amplifier 106 generates an amplified output signal 218 by amplifying electrical output signal 200. Similarly, a plurality of amplified output signals 220, 222, 224, 226, 228, and 230 are generated. An analog-to-digital converter converts an output signal from an analog form to a digital form to generate a digital output signal. For example, analog-to-digital converter 120 converts electrical output signal 196 from an analog form to a digital format to generate a digital output signal 232 and analog-to-digital converter 122 converts amplified output signal 216 from an analog form to a digital format to generate a digital output signal 234. Similarly, a plurality of digital output signals 236, 238, 240, 242, 244, 246, and 248 are generated by analog-to-digital converters 124, 126, 128, 130, 132, 134, and 136, respectively. A digital value of a digital output signal generated by an analog-to-digital converter represents an amplitude of energy of a pulse of an amplified output signal. Each pulse is generated by an x-ray quantum, such as an x-ray photon. For example, a digital value of digital output signal 234 output by analog-to-digital converter 122 is a value of an amplitude of a pulse of amplified output signal 216.

An adder of a spectrum memory circuit adds a number of pulses in a digital output signal. For example, when analog-to-digital converter 122 converts a pulse of amplified output signal 216 into digital output signal 234 to determine an amplitude of the pulse of amplified output signal 216, an adder within spectrum memory circuit 140 increments, by one, a value within a memory device of spectrum memory circuit 140. Accordingly, at an end of an x-ray examination of substance 82, a memory device within a spectrum memory circuit stores a number of x-ray quanta detected by a detector element. For example, a memory device within spectrum memory circuit 142 stores a number of x-ray photons detected by detector element 24 and each of the x-ray photons has an amplitude of energy or alternatively an amplitude of intensity that is determined by analog-to-digital converter 124.

A correction device receives a number of x-ray quanta that have a range of energies and are stored within a memory device of one of spectrum memory circuits 140, 142, 144, 146, 148, 150, 152, and 154, and divides the number by a number of x-ray quanta having the range of energies received from a memory device of spectrum memory circuit 138. For example, correction device 156 receives a number of x-ray photons having a range of energies from a memory device of spectrum memory circuit 140, and divides the number by a number of x-ray photons having the range received from a memory device of spectrum memory circuit 138. Each correction device outputs a correction output signal that represents a range of energies within x-ray quanta received by a detector element. For example, correction device 156 outputs a correction output signal 280 representing an energy spectrum or alternatively an intensity spectrum within x-ray quanta detected by detector element 22. As another example, correction device 158 outputs correction output signal 282 representing an energy spectrum within x-ray quanta detector element 24. Similarly, a plurality of correction output signals 284, 286, 288, 290, 292, and 294 are generated by correction devices 160, 162, 164, 166, 168, and 170, respectively.

It is noted that a number of pulse-height shaper amplifiers 104, 106, 108, 110, 112, 114, 116, and 118 changes with a number of scatter detector elements 22, 24, 26, 28, 30, 32, 34, and 36. For example, five pulse-height shaper amplifiers are used for amplifying signals received from five scatter detector elements. As another example, four pulse-height shaper amplifiers are used for amplifying signals received from four scatter detector elements. Similarly, a number of analog-to-digital converters 120, 122, 124, 126, 128, 130, 132, 134, and 136 changes with a number of detector elements 20, 22, 24, 26, 28, 30, 32, 34, and 36 and a number of spectrum memory circuits 138, 140, 142, 144, 146, 148, 150, 152, and 154 changes with the number of detector elements 20, 22, 24, 26, 28, 30, 32, 34, and 36.

Figure 3:
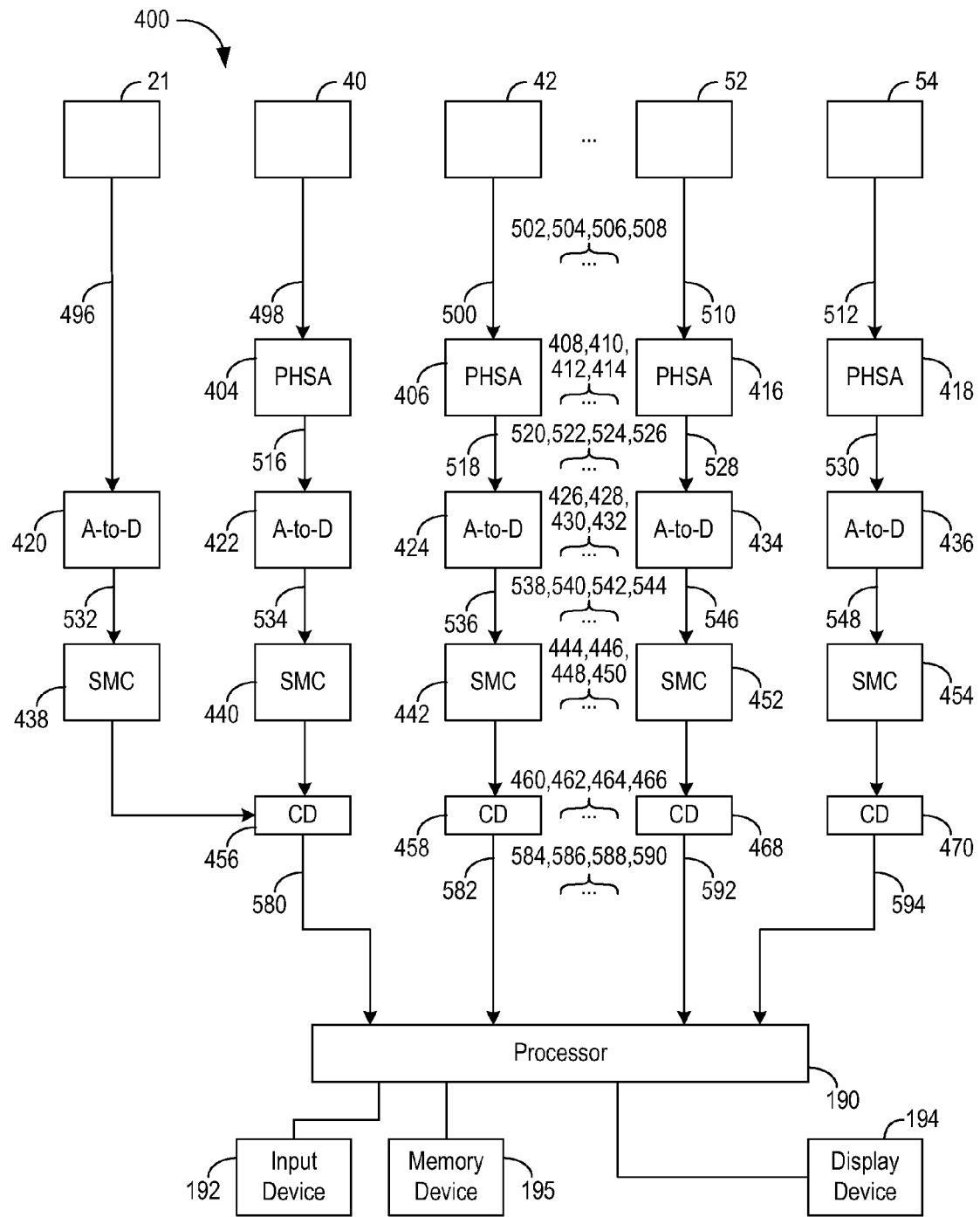
FIG. 3 is a block diagram of an embodiment of a system for generating an improved diffraction profile of a substance.

FIG. 3 is a diagram of an embodiment of a system 400 for generating an improved diffraction profile of a substance. System 400 includes detector element 21 of transmission detector 17, scatter detector elements 40, 42, 44, 46, 48, 50, 52, and 54, a plurality of pulse-height shaper amplifiers (PHSA) 404, 406, 408, 410, 412, 414, 416, and 418, a plurality of analog-to-digital (A-to-D) converters 420, 422, 424, 426, 428, 430, 432, 434, and 436, a plurality of spectrum memory circuits (SMCs) 438, 440, 442, 444, 446, 448, 450, 452, and 454 allowing pulse height spectra to be acquired, a plurality of correction devices (CDs) 456, 458, 460, 462, 464, 466, 468, and 470, processor 190, input device 192, display device 194, and memory device 195. An example of each of correction devices 456, 458, 460, 462, 464, 466, 468, and 470 include a divider circuit. Each of spectrum memory circuits 438, 440, 442, 444, 446, 448, 450, 452, and 454 include an adder and a memory device, such as a RAM or a ROM.

Transmission detector element 21 generates an electrical output signal 496 by detecting primary beam 84 and scatter detector elements 40, 42, 44, 46, 48, 50, 52, and 54 generate a plurality of electrical output signals 498, 500, 502, 504, 506, 508, 510, and 512 by detecting scattered radiation. For example, transmission detector element 21 generates electrical output signal 496 for x-ray photons incident on transmission detector element 21. Scatter detector elements 40, 42, 44, 46, 48, 50, 52, and 54 are coupled to pulse-height shaper amplifiers 404, 406, 408, 410, 412, 414, 416, and 418, respectively. Each pulse-height shaped amplifier amplifies an electrical output signal received from a detector element. For example, pulse-height shaper amplifier 404 amplifies electrical output signal 498. Pulse-height shaper amplifiers 404, 406, 408, 410, 412, 414, 416, and 418 have a gain factor determined by processor 190.

An amplitude of an electrical output signal output from a detector element is proportional to an energy of an x-ray quantum that is detected by the detector element to generate the electrical output signal. For example, an amplitude of electrical output signal 496 is proportional to an energy of an x-ray quantum in primary beam 84 detected by detector element 21. As another example, an amplitude of electrical output signal 498 is proportional to an energy of an x-ray quantum within scattered radiation that is detected by detector element 40.

A pulse-height shaper amplifier generates an amplified output signal by amplifying an electrical output signal generated from a detector element. For example, pulse-height shaper amplifier 404 generates an amplified output signal 516 by amplifying electrical output signal 498 and pulse-height shaper amplifier 406 generates an amplified output signal 518 by amplifying electrical output signal 500. Similarly, a plurality of amplified output signals 518, 520, 522, 524, 526, 528, and 530 are generated. An analog-to-digital converter converts an output signal from an analog form to a digital form to generate a digital output signal. For example, analog-to-digital converter 420 converts electrical output signal 496 from an analog form to a digital format to generate a digital output signal 532 and analog-to-digital converter 422 converts amplified output signal 516 from an analog form to a digital format to generate a digital output signal 534. Similarly, a plurality of digital output signals 536, 538, 540, 542, 544, 546, and 548 are generated by analog-to-digital converters 424, 426, 428, 430, 432, 434, and 436, respectively. A digital value of a digital output signal generated by an analog-to-digital converter represents an amplitude of energy or alternatively an amplitude of intensity of a pulse of an amplified output signal. Each pulse is generated by an x-ray quantum, such as an x-ray photon. For example, a digital value of digital output signal 534 output by analog-to-digital converter 422 is a value of an amplitude of a pulse of amplified output signal 516.

An adder of a spectrum memory circuit adds a number of pulses in a digital output signal. For example, when analog-to-digital converter 422 converts a pulse of amplified output signal 516 into digital output signal 534 to determine an amplitude of the pulse of amplified output signal 516, an adder within spectrum memory circuit 440 increments, by one, a value within a memory device of spectrum memory circuit 440. Accordingly, at an end of an x-ray examination of substance 82, a memory device within a spectrum memory circuit stores a number of x-ray quanta detected by a detector element. For example, a memory device within spectrum memory circuit 442 stores a number of x-ray photons detected by detector element 42 and each of the x-ray photons has an amplitude of energy that is determined by analog-to-digital converter 424.

A correction device receives a number of x-ray quanta that have a range of energies and are stored within a memory device of one of spectrum memory circuits 440, 442, 444, 446, 448, 450, 452, and 454, and divides the number by a number of x-ray quanta having the range of energies received from a memory device of spectrum memory circuit 438. For example, correction device 456 receives a number of x-ray photons having a range of energies from a memory device of spectrum memory circuit 440, and divides the number by a number of x-ray photons having the range received from a memory device of spectrum memory circuit 438. Each correction device outputs a correction output signal that represents a range of energies within x-ray quanta received by a detector element. For example, correction device 456 outputs a correction output signal 580 representing an energy spectrum or alternatively an intensity spectrum within x-ray quanta detected by detector element 40. As another example, correction device 458 outputs correction output signal 582 representing an energy spectrum within x-ray quanta detected by detector element 42. Similarly, a plurality of correction output signals 584, 586, 588, 590, 592, and 594 are generated by correction devices 460, 462, 464, 466, 468, and 470, respectively.

Processor 190 receives correction output signals 280, 282, 284, 286, 288, 290, 292, 294, 580, 582, 584, 586, 588, 590, 592, and 594 to generate a momentum transfer $x_A$, measured in inverse nanometers ($nm^{-1}$), from an energy spectrum $r(E_A)$ of energy $E_A$ of x-ray quanta within scattered radiation detected by scatter detectors 16 and 18 (FIG. 1). Processor 190 generates the momentum transfer $x_A$ by applying $$x_A = (E_A/hc)\sin(\theta/2) \quad (1)$$

where c is a speed of light, h is Planck's constant, θ represents constant scatter angles of x-ray quanta of scattered radiation detected by scatter detectors 16 and 18 (FIG. 1). Examples of θ include scatter angles 96 and 97 (FIG. 1). Processor 190 relates the energy $E_A$ to the momentum transfer $x_A$ by equation (1). Mechanical dimensions of secondary collimator 76 (FIG. 1) defines the scatter angle θ. The secondary collimator 76 (FIG. 1) restricts scattered radiation that does not have the angle θ. Processor 190 receives the scatter angle θ from a user, such as a human being, via input device 192. Processor 190 generates a diffraction profile of substance 82 (FIG. 1) by calculating a number of scatter x-ray photons that are detected by scatter detectors 16 and 18 and by plotting the number versus the momentum transfer $x_A$.

It is noted that a number of pulse-height shape amplifiers 404, 406, 408, 410, 412, 414, 416, and 418 changes with a number of scatter detector elements 40, 42, 44, 46, 48, 50, 52, and 54. For example, five pulse-height shaper amplifiers are used for amplifying signals received from five scatter detector elements. As another example, four pulse-height shaper amplifiers are used for amplifying signals received from four scatter detector elements. Similarly, a number of analog-to-digital converters 420, 422, 424, 426, 428, 430, 432, 434, and 436 changes with a number of detector elements 21, 40, 42, 44, 46, 48, 50, 52, and 54, and a number of spectrum memory circuits 438, 440, 442, 444, 446, 448, 450, 452, and 454 changes with the number of detector elements 21, 40, 42, 44, 46, 48, 50, 52, and 54.

Figure 4:
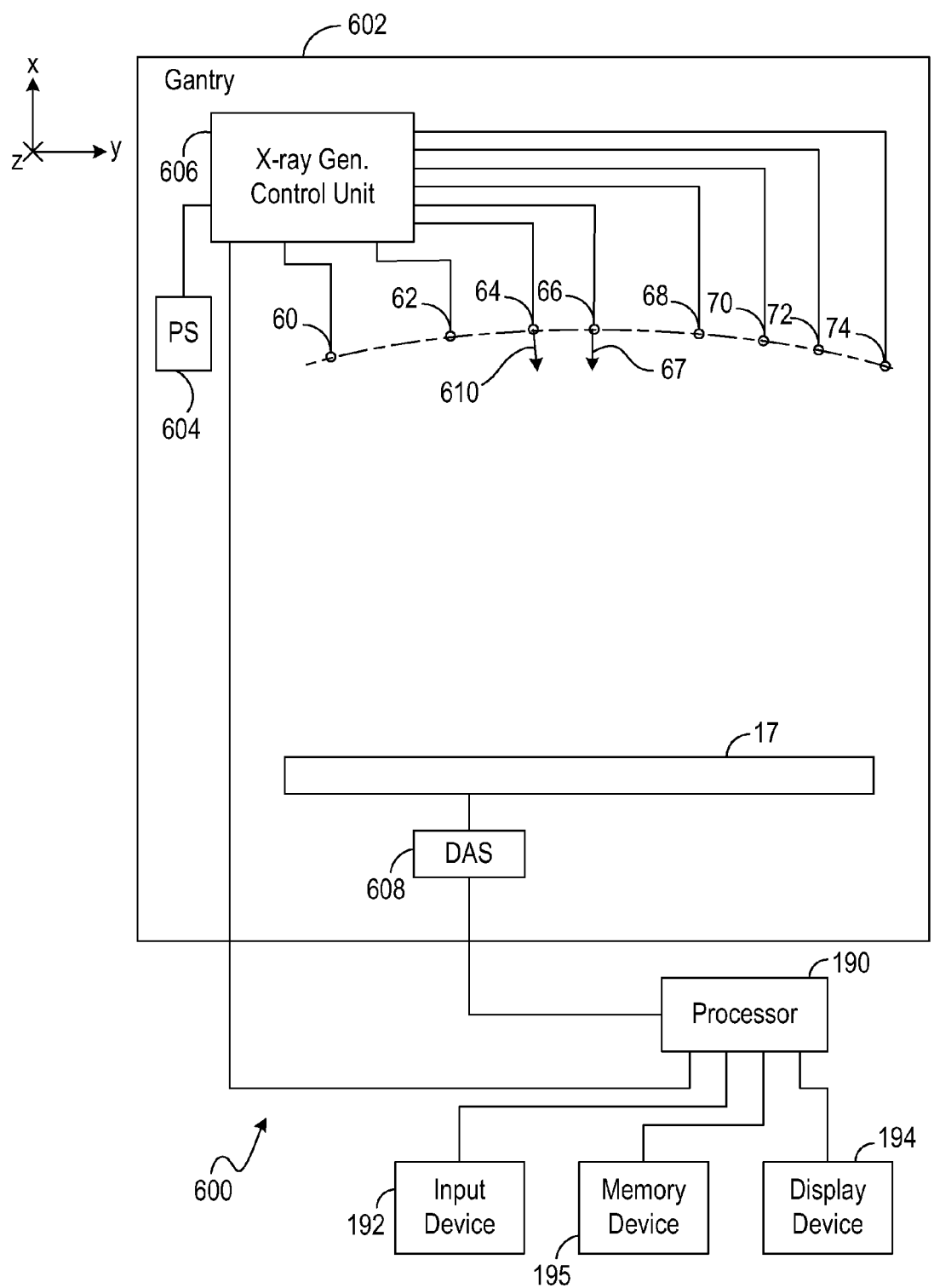
FIG. 4 is a block diagram of an embodiment of a system for generating an x-ray image.

FIG. 4 is a diagram of an embodiment of a system 600 for generating an x-ray image. System 600 includes a gantry 602, processor 190, input device 192, display device 194, and memory device 195. Gantry 602 is an example of gantry 12 (FIG. 1). Gantry 602 includes a power supply 604, an x-ray generation control unit 606, x-ray sources 60, 62, 64, 66, 68, 70, 72, and 74, a data acquisition system (DAS) 608, and transmission detector 17. Alternatively, power supply 604 is located outside gantry 602.

X-ray generation control unit 606 includes a pulse generator (not shown) that is coupled to processor 190 and that receives power from power supply 604. Power supply 604 is coupled to x-ray sources 60, 62, 64, 66, 68, 70, 72, and 74 to supply power to x-ray sources 60, 62, 64, 66, 68, 70, 72, and 74.

Processor 190 issues a command, such as a first on command, a second on command, a first off command, and a second off command. Upon receiving the first on command from processor 190, the pulse generator generates a pulse and transmits the pulse to x-ray source 66. Upon receiving a pulse from the pulse generator, x-ray source 66 generates x-ray beam 67 under a potential applied by power supply 604. Similarly, upon receiving the first off command signal from processor 190, the pulse generator stops transmitting a pulse to x-ray source 66 and x-ray source 66 stops generating x-ray beam 67. Furthermore, upon receiving the second on command signal from processor 190, the pulse generator generates and transmits a pulse to any one of the remaining x-ray sources 60, 62, 64, 68, 70, 72, and 74 and any one of the remaining x-ray sources 60, 62, 64, 68, 70, 72, and 74 generates an x-ray beam. For example, upon receiving the second on command signal from processor 190, the pulse generator generates and transmits a pulse to x-ray source 64 and x-ray source 64 generates an x-ray beam 610. Upon receiving the second off command signal from processor 190, the pulse generator stops transmitting a pulse to any one of the remaining x-ray sources 60, 62, 64, 68, 70, 72, and 74 and the one of the remaining x-ray sources 60, 62, 64, 68, 70, 72, and 74 stops generating an x-ray beam.

DAS 608 samples analog data, such as electrical output signals, generated from a plurality of detector elements, including detector elements 20 and 21, of transmission detector 17 and converts the analog data to a plurality of digital signals for subsequent processing.

Figure 5:
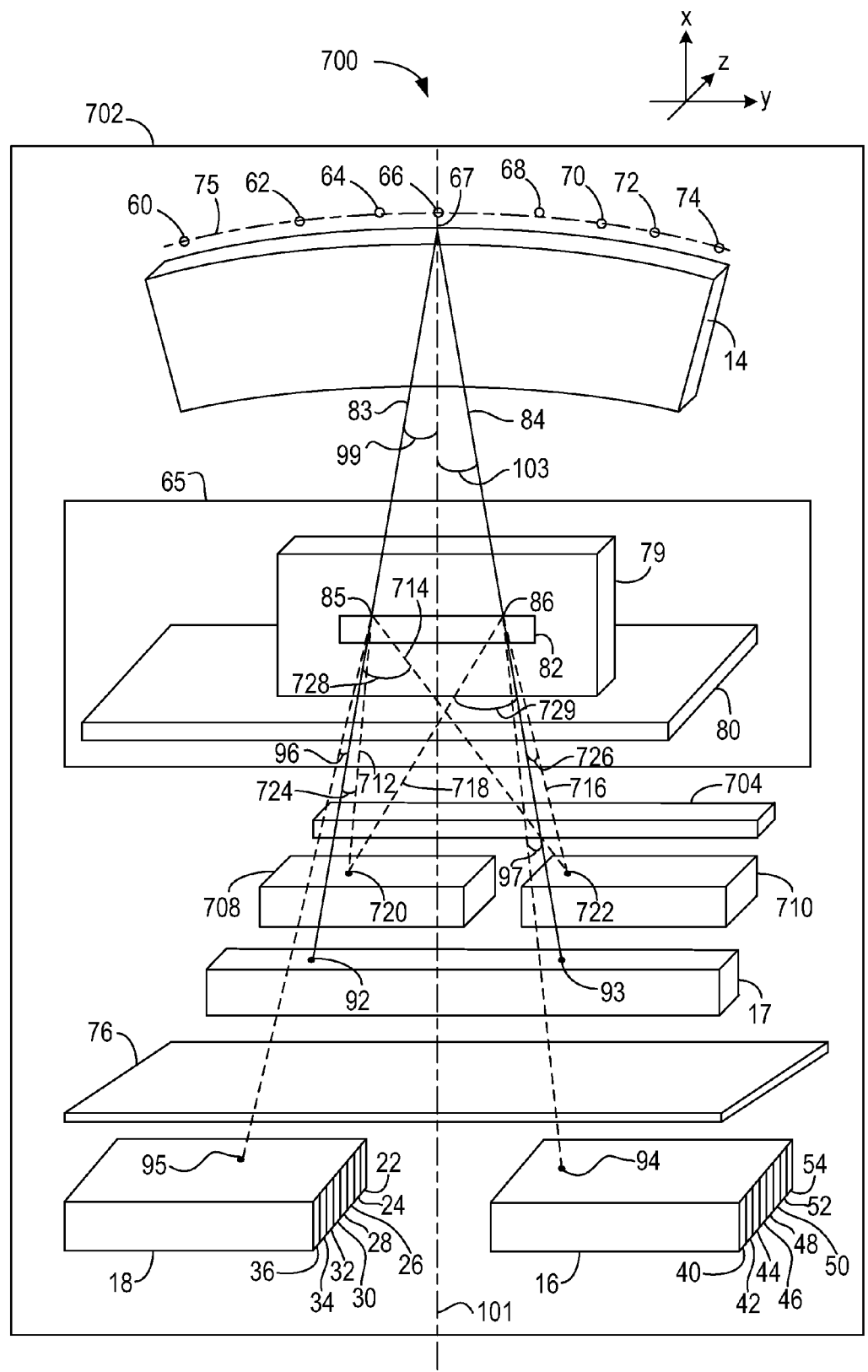
FIG. 5 is an isometric view of an alternative embodiment of a system for generating an improved diffraction profile of a substance.

FIG. 5 is an isometric view of an alternative embodiment of a system 700 for generating a diffraction profile of a substance. System 700 includes a gantry 702. Gantry 702 includes x-ray sources 60, 62, 64, 66, 68, 70, 72, and 74, primary collimator 14, secondary collimator 76, scatter detectors 16 and 18, transmission detector 17, a secondary collimator 704, and a plurality of scatter detectors 708 and 710 that detect coherent scatter. Gantry 702 is an example of gantry 12 (FIG. 1). Secondary collimator 704 has the same structure as that of secondary collimator 76. Scatter detectors 708 and 710 are located on a side of transmission detector 17 and the side is opposite to a side where scatter detectors 16 and 18 are located. A number of scatter detectors on a side, with respect to transmission detector 17, of placement of scatter detectors 16 and 18 is the same as a number of scatter detectors on a side, with respect to transmission detector 17, of placement of scatter detectors 708 and 710. For example, if five scatter detectors are placed on one side of transmission detector 17 where scatter detectors 16 and 18 are placed, five scatter detectors are placed on the other side of transmission detector 17 where scatter detectors 708 and 710 are placed. A shortest distance between a center of scatter detector 708 and a center of scatter detector 710 is the same as shortest distance 56 between a center of scatter detector 16 and a center of scatter detector 18. Scatter detectors 708 and 710 are separated from each other by a gap. Each scatter detector 708 and 710 has the same number of detector elements as scatter detector 16. A shortest distance of transmission detector 17 from any of scatter detectors 16, 18, 708, and 710 is the same. For example, a shortest distance of transmission detector 17 from scatter detector 708 is equal to the shortest distance of transmission detector 17 from scatter detector 18.

Primary beams 83 and 84 pass through points 85 and 86 on substance 82 to generate scattered radiation 88 (FIG. 1), 89 (FIG. 1), 90 (FIG. 1), 91 (FIG. 1), 712, 714, 716, and 718. For example, primary beam 83 passes through point 85 on substance 82 to generate scattered radiation 88 (FIG. 1), 89 (FIG. 1), 712 and 714. As another example, primary beam 84 passes through point 86 on substance 82 to generate scattered radiation 90 (FIG. 1), 91 (FIG. 1), 716 and 718.

Secondary collimator 704 is located between support 80 and a set of scatter detectors 708 and 710. Secondary collimator 704 includes a number of collimator elements to ensure that scattered radiation arriving at scatter detectors 708 and 710 have constant scatter angles with respect to primary beams 83 and 84 and that a position of scatter detectors 708 and 710 permits a depth in container 79 at which the scattered radiation originated to be determined. For example, the collimator elements of secondary collimator 704 are arranged parallel to a direction of scattered radiation 712 and of scattered radiation 716 to absorb scattered radiation that is not parallel to the direction of scattered radiation 712 and of scattered radiation 716.

The number of collimator elements in secondary collimator 704 provided is equal to or alternatively greater than a number of detector elements of one of scatter detectors 708 and 710 and the collimator elements are arranged such that scattered radiation between neighboring collimator elements is incident on one of the detector elements. The collimator elements of scatter detectors 708 and 710 are made of a radiation-absorbing material, such as, a copper alloy or a silver alloy.

Underneath support 80, there are arranged scatter detectors 708 and 710 that measure photon energies of scattered radiation detected by scatter detectors 708 and 710. Scatter detectors 16, 18, transmission detector 17, and scatter detectors 708 and 710 lie in the same yz plane. Each of scatter detectors 708 and 710 measures the x-ray photons within scattered radiation in an energy-sensitive manner by outputting a plurality of electrical output signals linearly dependent on a plurality of energies of the x-ray photons detected from within scattered radiation. Scatter detector 708 measures scattered radiation 712 received at a point 720 on scatter detector 708 and scatter detector 710 measures scattered radiation 716 received at a point 722 on scatter detector 710. An example of a shortest distance between points 85 and 720 includes a distance ranging from and including 900 mm to 1100 mm. An example of a distance between points 720 and 92 includes a distance ranging from and including 25 mm to 45 mm.

Scatter detectors 708 and 710 detect scattered radiation to generate a plurality of electrical output signals. Scatter detector 708 detects scattered radiation 712 generated upon intersection of primary beam 83 with point 85. Moreover, scatter detector 708 detects scattered radiation 718 generated upon intersection of primary beam 84 with point 86. Scatter detector 710 detects scattered radiation 716 generated upon intersection of primary beam 84 with point 86. Moreover, scatter detector 710 detects scattered radiation 714 generated upon intersection of primary beam 83 with point 85. A scatter angle 724 formed between primary beam 83 and scattered radiation 712 is equal to a scatter angle 726 formed between primary beam 84 and scattered radiation 716. An example of each of scatter angles 724 and 726 includes an angle ranging from and including 0.025 radians to 0.045 radians. An example of a scatter angle 728 formed between primary beam 83 and scattered radiation 714 ranges from and including 0.05 radians to 0.09 radians. Moreover, an example of a scatter angle 729 formed between primary beam 84 and scattered radiation 718 ranges from and including 0.05 radians to 0.09 radians. Scatter angle 728 is at least twice of each scatter angle 724 and 726 and scatter angle 729 is at least twice of each scatter angle 724 and 726. Angle 99 formed by primary beam 83 with respect to center 101 between scatter detectors 708 and 710 is equal to angle 103 formed by primary beam 84 with respect to center 101. In an alternative embodiment, system 700 does not include secondary collimators 76 and 704.

Scatter detector 708 is connected to a system similar to system 100 (FIG. 2) to generate a plurality of correction output signals, such as correction output signals 280, 282, 284, 286, 288, 290, 292, and 294 (FIG. 2). Moreover, scatter detector 710 is connected to a system similar to system 400 (FIG. 3) to generate a plurality of correction output signals, such as correction output signals 580, 582, 584, 586, 588, 590, 592, and 594 (FIG. 3). Processor 190 receives correction output signals 280, 282, 284, 286, 288, 290, 292, 294, 580, 582, 584, 586, 588, 590, 592, and 594 (FIGS. 2 and 3), the correction output signals generated by the system that is similar to system 100 (FIG. 2) and that is connected to scatter detector 708, and the correction output signals generated by the system that is similar to system 400 (FIG. 3) and that is connected to scatter detector 710, to generate a momentum transfer $x_B$.

Processor 190 generates the momentum transfer $x_B$, measured in $nm^{-1}$, from an energy spectrum $r(E_B)$ of energy $E_B$ of x-ray quanta within scattered radiation detected by scatter detectors 16, 18, 708, and 710. Processor 190 generates the momentum transfer $x_B$ by applying $$x_B = (E_B/hc)\sin(\theta/2) \qquad (2)$$

where c is a speed of light, h is Planck's constant, θ represents constant scatter angles of x-ray quanta of scattered radiation detected by scatter detectors 16, 18, 708, and 710. Examples of θ include scatter angles 96 (FIG. 1), 97 (FIG. 1), 724, and 726. Processor 190 relates the energy $E_B$ to the momentum transfer $x_B$ by equation (2). The secondary collimators 76 (FIG. 1) and 704 restrict scattered radiation that does not have the angle θ. Processor 190 generates a diffraction profile of substance 82 by calculating a number of scatter x-ray photons that are detected by scatter detectors 16, 18, 708 and 710, and by plotting the number versus the momentum transfer $x_B$.

Figure 6:
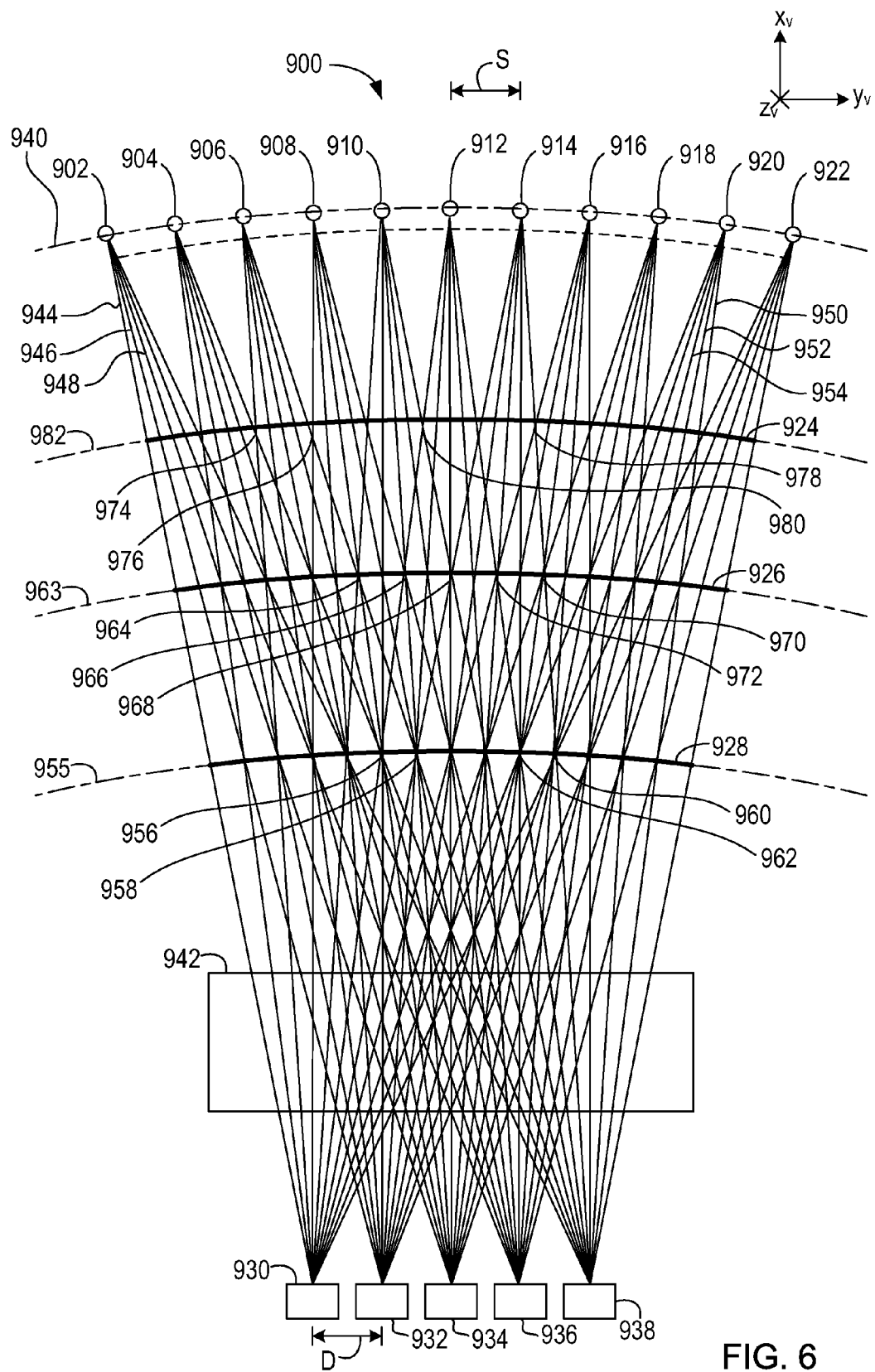
FIG. 6 is a diagram of illustrating an embodiment of a virtual system for developing a primary collimator of the system of FIG. 1.

FIG. 6 is a diagram of illustrating an embodiment of a virtual system 900 for developing a primary collimator. Processor 190 generates virtual system 900. For example, processor 190 generates virtual system 900 to display virtual system 900 on display device 194 (FIG. 2). Virtual system 900 includes a plurality of virtual x-ray sources 902, 904, 906, 908, 910, 912, 914, 916, 918, 920, and 922, a plurality of virtual collimator elements 924, 926, and 928, and a plurality of virtual detectors 930, 932, 934, 936, and 938, such as virtual transmission detectors. Processor 190 generates virtual x-ray sources 906, 908, 910, 912, 914, 916, 918, and 920 as a virtual representation of x-ray sources 60, 62, 64, 66, 68, 70, 72, and 74 (FIG. 1) and locates virtual x-ray sources 902, 904, 906, 908, 910, 912, 914, 916, 918, 920, and 922 along a curve 940. Processor 190 generates each of remaining virtual x-ray sources 902, 904, and 922 (FIG. 1) as a virtual representation of an x-ray source, such as x-ray source 74. Moreover, processor 190 generates virtual detector 934 as a virtual representation of transmission detector 17 (FIG. 1). Processor 190 generates each of remaining virtual detectors 930, 932, 936, and 938 as a virtual representation of a transmission detector, such as transmission detector 17. Processor 190 generates a virtual opening 942 as a virtual representation of opening 65 (FIG. 1).

The user provides an organization of the components of system 10 (FIG. 1) to processor 190 via input device 192 (FIG. 2). The user inputs, via input device 192, a plurality of distances between the components of system and provides the organization of the components of system 10 to processor 190 by providing the distances to processor 190 via input device 192. For example, the user specifies a number of detector elements within transmission detector 17, a number of detector elements within each of scatter detectors 16 and 18, a radius of arc 75, a plurality of positions of x-ray sources 60, 62, 64, 66, 68, 70, 72, and 74 with respect to at least one of transmission detector 17, scatter detector 16, and scatter detector 18, a distance between any two of x-ray sources 60, 62, 64, 66, 68, 70, 72, and 74, and a position of opening 65 with respect to at least one of transmission detector 17, scatter detector 16, and scatter detector 18, and x-ray source 66.

Processor 190 organizes the virtual elements of virtual system 900 and the organization is proportional, by a first factor, such as one-half or one-third, to the organization of the components of system 10 input by the user. For example, processor 190 generates any two of adjacent virtual x-ray sources from virtual x-ray sources 902, 904, 906, 908, 910, 912, 914, 916, 918, 920, and 922 and a distance between the two adjacent virtual x-ray sources is proportional, such as one-half or one-third, to a distance between any two adjacent x-ray sources from x-ray sources 60, 62, 64, 66, 68, 70, 72, and 74. As another example, processor 190 generates two adjacent virtual detectors from virtual detectors 930, 932, 934, 936, and 938 and a distance between the two adjacent virtual detectors is proportional to a distance between transmission detector 17 (FIG. 1) and another transmission detector (not shown) adjacent to transmission detector 17 (FIG. 1). As yet another example, processor 190 generates virtual x-ray source 912 and virtual detector 934, and a distance between virtual x-ray source 912 and virtual detector 934 is proportional to a distance between x-ray source 66 and transmission detector 17. As still another example, processor 190 generates virtual opening 942 and a distance between virtual opening 942 and virtual x-ray source 912 is proportional to a distance between x-ray source 66 and opening 65. As a further example, processor 190 generates virtual detector 934 and a distance between virtual detector 934 and virtual opening 942 is proportional to a distance between transmission detector 17 and opening 65.

Processor 190 extends a number, such as four or five, of virtual beams, which are straight lines, from each virtual x-ray source 902, 904, 906, 908, 910, 912, 914, 916, 918, 920, and 922. Processor 190 extends the number of virtual beams and the number matches a number of virtual detectors 930, 932, 934, 936, and 938. For example, processor 190 extends five virtual beams from each virtual x-ray source 902, 904, 906, 908, 910, 912, 914, 916, 918, 920, and 922 and upon organizing five virtual detectors 930, 932, 934, 936, and 938 within virtual system 900. As another example, processor 190 extends four virtual beams from each virtual x-ray source 902, 904, 906, 908, 910, 912, 914, 916, 918, 920, and 922 and upon organizing four virtual detectors within virtual system 900.

Processor 190 extends the number of virtual beams from each virtual x-ray source 902, 904, 906, 908, 910, 912, 914, 916, 918, 920, and 922 and each virtual detector 930, 932, 934, 936, and 938 receives one of the virtual beams. For example, processor 190 extends a virtual beam 944, as a straight line, from virtual x-ray source 902 and virtual detector 930 receives virtual beam 944. As another example, processor 190 extends a virtual beam 946, as a straight line, from virtual x-ray source 902 and virtual detector 932 receives virtual beam 946. As yet another example, processor 190 extends a virtual beam 948, as a straight line, from virtual x-ray source 902 and virtual detector 934 receives virtual beam 948. As still another example, processor 190 extends a virtual beam 950, as a straight line, from virtual x-ray source 920 and processor 190 and virtual detector 938 receives virtual beam 950. As another example, processor 190 extends a virtual beam 952, as a straight line, from virtual x-ray source 920 and virtual detector 936 receives virtual beam 952. As yet another example, processor 190 extends a virtual beam 954, as a straight line, from virtual x-ray source 920 and virtual detector 934 receives virtual beam 954.

Processor 190 determines a number of virtual points between virtual x-ray sources 902, 904, 906, 908, 910, 912, 914, 916, 918, 920, and 922 and virtual detectors 930, 932, 934, 936, and 938 and a maximum number, such as 5 or 6, of virtual beams intersect each other at each of the virtual points. As an example, processor 190 determines that five virtual beams from virtual x-ray sources 904, 906, 908, 910, and 912 intersect each other at a virtual point 956. As another example, processor 190 determines that five virtual beams from virtual x-ray sources 906, 908, 910, 912, and 914 intersect each other at a virtual point 958. The maximum number is equal to the number of virtual beams output by each virtual x-ray source 902, 904, 906, 908, 910, 912, 914, 916, 918, 920, and 922. Similarly, processor 190 determines virtual points 960 and 962. Processor 190 generates an axis 955 that extends through virtual points 956, 958, 960, and 962. Processor 190 generates virtual collimator element 928 that coincides with axis 955 at a plurality of virtual points, such as virtual points 956, 958, 960, and 962. In an alternative embodiment, processor 190 generates a lower or alternatively a higher number of virtual points on axis 955 than a number of virtual points 956, 958, 960, and 962.

Processor 190 determines a number of virtual points between virtual x-ray sources 902, 904, 906, 908, 910, 912, 914, 916, 918, 920, and 922 and virtual detectors 930, 932, 934, 936, and 938 and a number, such as three, lower than the maximum number, of virtual beams intersect each other at each of the virtual points. As an example, processor 190 determines that three virtual beams from virtual x-ray sources 906, 908, and 910 intersect each other at a virtual point 964. As another example, processor 190 determines that three virtual beams from virtual x-ray sources 908, 910, and 912 intersect each other at a virtual point 966. Similarly, processor 190 determines virtual points 968, 970, and 972. Processor 190 generates an axis 963 that extends through virtual points 964, 966, 968, 970, and 972. Processor 190 generates virtual collimator element 926 that coincides with axis 963 at a plurality of virtual points, such as virtual points 964, 966, 968, 970, and 972. As yet another example, processor 190 determines that two virtual beams from virtual x-ray sources 904 and 906 intersect each other at a virtual point 974. As another example, processor 190 determines that two virtual beams from virtual x-ray sources 906 and 908 intersect each other at a virtual point 976. Similarly, processor 190 determines virtual points 978 and 980. Processor 190 generates an axis 982 that extends through virtual points 974, 976, 978, and 980. Processor 190 collates the intersection points to find those which pass through approximately the same x-position. Processor 190 generates virtual collimator element 924 that coincides with axis 982 at a plurality of virtual points, such as virtual points 974, 976, 978, and 980. Virtual collimator element 928 is closest to virtual opening 942 than the remaining virtual collimator elements 924 and 926. In an alternative embodiment, processor 190 generates a lower or alternatively a higher number of virtual points on axis 963 than a number of virtual points 964, 966, 968, 970, and 972. In another alternative embodiment, 190 generates a lower or alternatively a higher number of virtual points on axis 982 than a number of virtual points 974, 976, 978, and 980.

Processor 190 generates virtual collimator elements 924, 926, and 928 and virtual collimator elements 924, 926, and 928 do not intersect virtual opening 942. In an alternative embodiment, virtual collimator elements 924, 926, and 928 do not intersect container 79. Processor 190 generates virtual collimator elements 924, 926, and 928 that lie between virtual x-ray sources 902, 904, 906, 908, 910, 912, 914, 916, 918, 920, and 922 and virtual opening 942. Processor 190 determines a plurality of virtual positions, such as $x_{v1}$ and $y_{v1}$ virtual co-ordinates or $x_{v2}$ and $y_{v2}$ virtual co-ordinates or $x_{v3}$ and $y_{v3}$ virtual co-ordinates, of virtual collimator elements 924, 926, and 928 and determines a plurality of positions, such as $x_{v4}$ and $y_{v4}$ virtual co-ordinates, $x_{v5}$ and $y_{v5}$ virtual co-ordinates, $x_{v6}$ and $y_{v6}$ virtual co-ordinates, $x_{v7}$ and $y_{v7}$ virtual co-ordinates, $x_{v8}$ and $y_{v8}$ virtual co-ordinates, or $x_{v9}$ and $y_{v9}$ virtual co-ordinates, of virtual points on virtual collimator elements 924, 926, and 928. For example, processor 190 determines the $x_{v1}$ and $y_{v1}$ virtual co-ordinates of virtual collimator element 928 with respect to an origin of an $x_v y_v z_v$ co-ordinate system. As another example, processor 190 determines the $x_{v4}$ and $y_{v4}$ virtual co-ordinates of virtual point 974 with respect to the origin of the $x_v y_v z_v$ co-ordinate system. The $x_v y_v z_v$ co-ordinate system is proportional to the xyz co-ordinate system shown in FIGS. 1, 4, and 5. The $x_v y_v z_v$ co-ordinate system includes an $x_v$ axis, a $y_v$ axis, and a $z_v$ axis. The $x_v$ axis is perpendicular to the $y_v$ axis and the $z_v$ axis, and the $y_v$ axis is perpendicular to the $z_v$ axis.

It is noted that virtual collimator elements 924, 926, and 928 are curved and that none of virtual collimator elements 924, 926, and 928 are circular in shape. It is also noted that in an alternative embodiment, processor 190 generates virtual collimator element 928 and does not generate any other virtual collimator element. In yet another alternative embodiment, processor 190 generates any number, such as 2, 3, 4, or 5, of virtual collimator elements.

Figure 7:
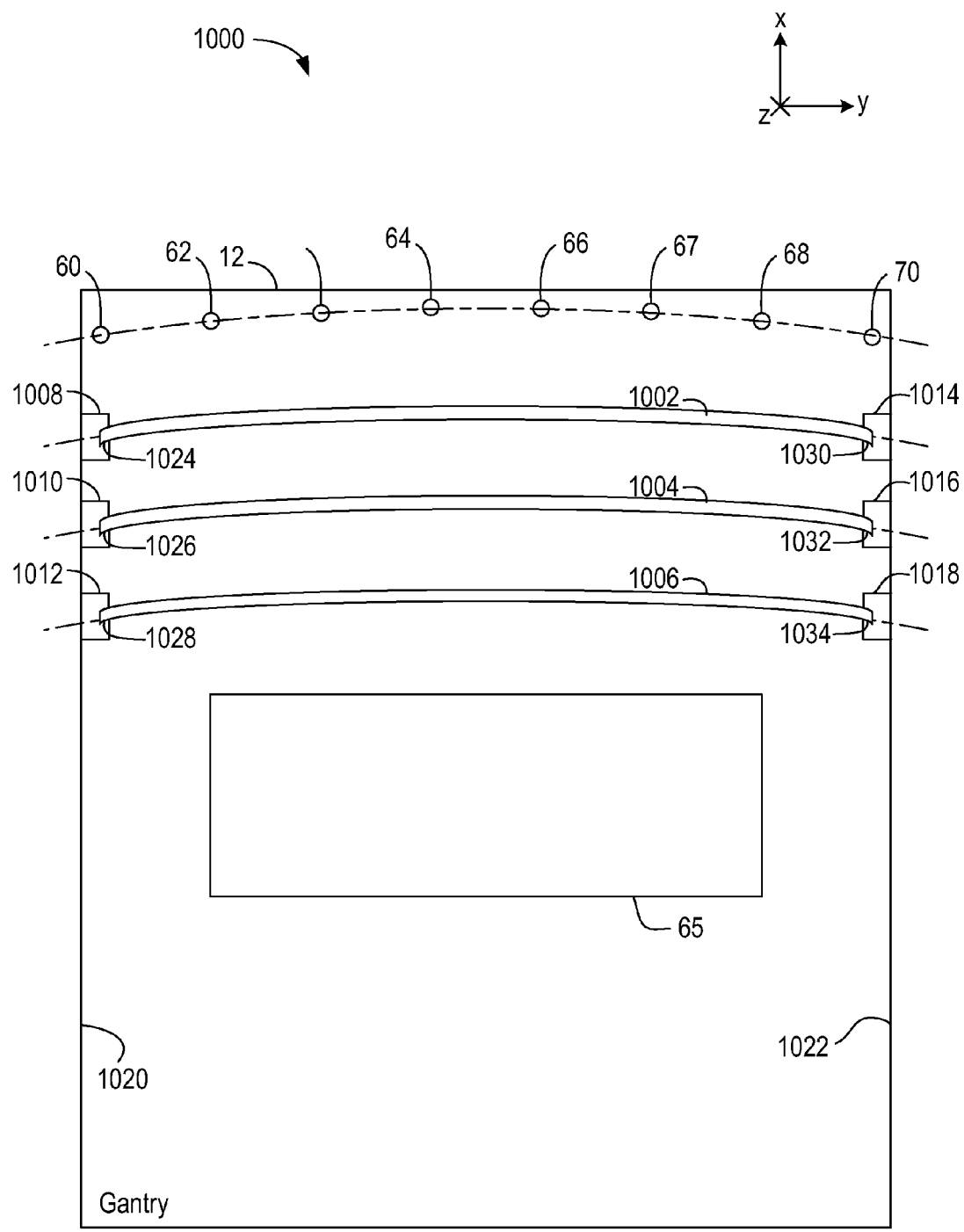
FIG. 7 is a diagram of an embodiment of a system implementing the primary collimator.

FIG. 7 is a diagram of an embodiment of a system 1000 implementing a primary collimator. System 1000 is an example of system 10 (FIG. 1) and system 600 (FIG. 4). Alternatively, system 1000 is an example of system 700 (FIG. 5). System 1000 includes gantry 12. Gantry 12 includes opening 65, x-ray sources 60, 62, 64, 66, 68, 70, 72, and 74, a plurality of primary collimator elements 1002, 1004, and 1006, and a plurality of holders 1008, 1010, 1012, 1014, 1016, and 1018. An example of each of primary collimator elements 1002, 1004, and 1006 include a sheet or a lamination. Primary collimator elements 1002, 1004, and 1006 are fabricated from a material, such as molybdenum or tungsten. Holders 1008, 1010, 1012, 1014, 1016, and 1018 are fabricated from a metal, such as steel or aluminum. Primary collimator elements 1002, 1004, and 1006 are located between x-ray sources 60, 62, 64, 66, 68, 70, 72, and 74 and opening 65, and collectively form primary collimator 14 (FIG. 1). As an example, each primary collimator element 1002, 1004, and 1006 has a length ranging from and including 1 meters (m) to 1.5 meters in the y-direction, ranging from and including 0.5 millimeters (mm) to 5 mm in the z-direction, and ranging from and including 2.5 mm to 5.5 mm in the x-direction.

Primary collimator element 1002 is supported by holders 1008 and 1014. Primary collimator element 1004 is support by holders 1010 and 1016, and primary collimator element 1006 is supported by holders 1012 and 1018. Holders 1008, 1010, 1012, 1014, 1016, and 1018 are attached by a connection process, such as gluing or spot welding, to a plurality of side walls 1020 and 1022 of gantry 12. For example, holders 1008, 1010, and 1012 are attached to side wall 1020 and holders 1014, 1016, and 1018 are attached to side wall 1022. Alternatively, holders 1008, 1010, 1012, 1014, 1016, and 1018 are attached to side walls 1020 and 1022 by fitting holders 1008, 1010, and 1012 to side wall 1020 via a plurality of screws and by fitting holders 1014, 1016, and 1018 to side wall 1022 via a plurality of screws. Each of holders 1008, 1010, 1012, 1014, 1016, and 1018 include a slot that extends in the z-direction. For example, holder 1008 includes a slot 1024, holder 1010 includes a slot 1026, holder 1012 includes a slot 1028, holder 1014 includes a slot 1030, holder 1016 includes a slot 1032, and holder 1018 includes a slot 1034.

The user fabricates holders 1008, 1010, 1012, 1014, 1016, and 1018 and slots 1024, 1026, 1028, 1030, 1032, and 1034 by using a molding machine having a plurality of peaks of a shape of any of slots 1024, 1026, 1028, 1030, 1032, and 1034, filling a liquid metal, such as steel, within the molding machine, and cooling the metal to create slots 1024, 1026, 1028, 1030, 1032, and 1034 within holders 1008, 1010, 1012, 1014, 1016, and 1018. Alternatively, the user creates slots 1024, 1026, 1028, 1030, 1032, and 1034 by operating an etching machine to develop slots 1024, 1026, 1028, 1030, 1032, and 1034. Each of slots 1024, 1026, 1028, 1030, 1032, and 1034 have a plurality of dimensions that are slightly larger than a plurality of dimensions of each of primary collimator elements 1002, 1004, and 1006. For example, if primary collimator element 1002 has a dimension along the x-axis of 5 mm, slot 1024 has a dimension along the x-axis of more than 5 mm, such as 5.2 mm. As another example, if primary collimator element 1002 has a dimension along the y-axis of 1.2 m, slot 1024 has a dimension along the y-axis of more than 1.2 m, such as 1.5 m. As yet another example, if primary collimator element 1002 has a dimension along the z-axis of 1 mm, slot 1024 has a dimension along the y-axis of more than 1.2 mm, such as 1.5 mm.

The user slides a primary collimator element within slots to use holders to support primary collimator element. For example, the user slides, in the z-direction, primary collimator element 1002 within slot 1024 of holder 1008 and slot 1030 of holder 1014 to use holders 1008 and 1014 to support primary collimator element 1002. As another example, the user slides, in the z-direction, primary collimator element 1004 within slot 1026 of holder 1010 and slot 1032 of holder 1016 to use holders 1010 and 1016 to support primary collimator element 1004.

Processor 190 calculates a plurality of positions, such as $x_1$ and $y_1$ co-ordinates, $x_2$ and $y_2$ co-ordinates, or $x_3$ and $y_3$ co-ordinates, of primary collimator elements 1002, 1004, and 1006 within gantry 12 as being proportional, by a second factor, such as 2 or 3, to the virtual positions of virtual collimator elements 924, 926, and 928. For example, processor 190 multiplies the co-ordinates $x_{v1}$ and $y_{v1}$ co-ordinates of virtual collimator element 928 with the second factor to generate the $x_1$ and $y_1$ co-ordinates of primary collimator element 1006. As another example, processor 190 multiplies the $x_{v2}$ and $y_{v2}$ co-ordinates of virtual collimator element 926 with the second factor to generate the $x_2$ and $y_2$ co-ordinates of primary collimator element 1004. As yet another example, processor 190 multiplies the $x_{v3}$ and $y_{v3}$ co-ordinates of virtual collimator element 924 with the second factor to generate the co-ordinates $x_3$ and $y_3$ of primary collimator element 1002. The second factor is an inverse of the first factor. For example, if the first factor is one-half, the second factor is 2.

Virtual collimator element 924 (FIG. 6) is a virtual representation of primary collimator element 1002, virtual collimator element 926 (FIG. 6) is a virtual representation of primary collimator element 1004, and virtual collimator element 928 (FIG. 6) is a virtual representation of primary collimator element 1006. Primary collimator 14 includes any number, such as 2, 3, or 4, of primary collimator elements, such as primary collimator elements 1002, 1004, and 1006. Primary collimator element 1006 has a minimum number of apertures compared to a number of apertures in either primary collimator element 1002 or primary collimator element 1004. It is advantageous to have primary collimator element 1006 with the minimum number of apertures. The minimum number of apertures depends on a size of container 79 and a number of x-ray sources for scanning container 79.

Figure 8:
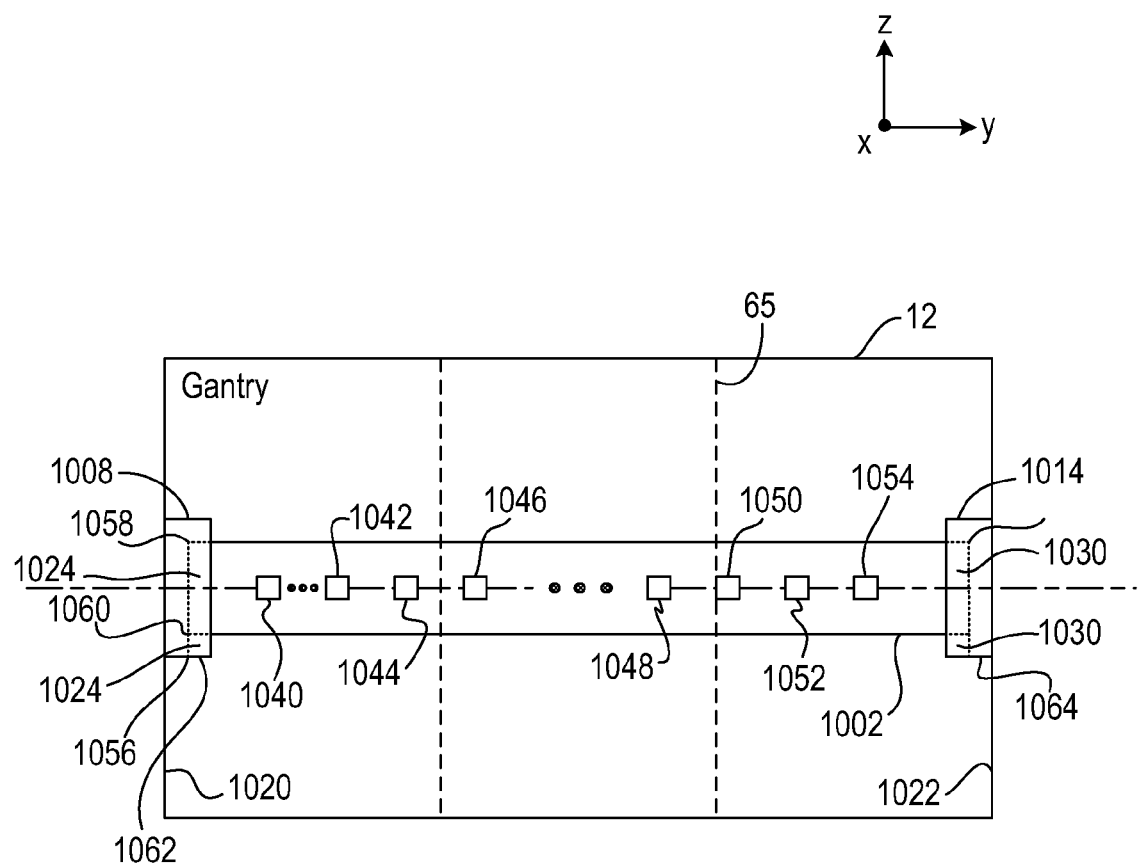
FIG. 8 is a top view of an embodiment of a gantry of the system of FIG. 1.

FIG. 8 is a top view of an embodiment of gantry 12. Gantry 12 includes primary collimator element 1002 and holders 1008 and 1014. Primary collimator element 1002 includes a plurality of apertures 1040, 1042, 1044, 1046, 1048, 1050, 1052, and 1054. A number of apertures within primary collimator element 1002 is equal to a number of virtual points on virtual collimator element 924. Processor 190 outputs a plurality of positions, such as the co-ordinates $x_4$ and $y_4$, of apertures within primary collimator element 1002 as being proportional by the second factor to the positions of virtual points of virtual collimator element 924. For example, processor 190 multiplies the virtual co-ordinates $x_{v4}$ and $y_{v4}$ of virtual point 974 with the second factor to generate the co-ordinates $x_4$ and $y_4$ of aperture 1042 of primary collimator element 1002. As another example, processor 190 multiplies the co-ordinates $x_{v5}$ and $y_{v5}$ of virtual point 976 with the second factor to generate a plurality of co-ordinates $x_5$ and $y_5$ of aperture 1044 of primary collimator element 1002.

Slot 1024 has a length in the z-direction greater than a length of primary collimator element 1002 in the z-direction. For example, slot 1024 extends, within holder 1008, from a point 1056 to a point 1058, along the z-direction and primary collimator element 1002 extends from a point 1060 to point 1058, along the z-direction. A distance, in the z-direction, between points 1058 and 1060 is less than a distance, in the z-direction, between points 1056 and 1058. The user slides, in the z-direction, primary collimator element 1002 from a side 1062 of holder 1008 into slot 1024 and from a side 1064 of holder 1014 into slot 1030 to locate primary collimator element 1002 within slots 1024 and 1030.

Figure 9:
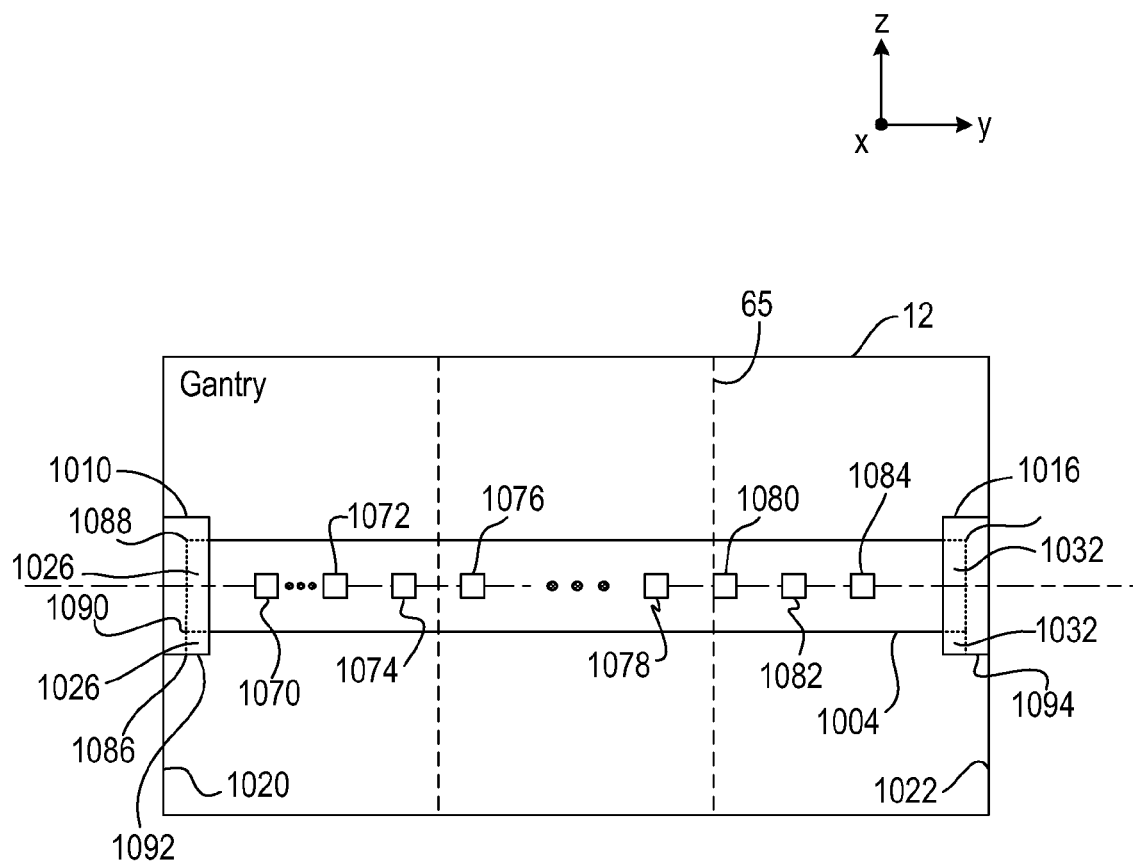
FIG. 9 is another top view of an embodiment of the gantry.

FIG. 9 is a top view of an embodiment of gantry 12. Gantry 12 includes primary collimator element 1004 and holders 1010 and 1016. Primary collimator element 1004 includes a plurality of apertures 1070, 1072, 1074, 1076, 1078, 1080, 1082, and 1084. A number of apertures within primary collimator element 1004 is equal to a number of virtual points on virtual collimator element 926. Processor 190 outputs a plurality of positions, such as the co-ordinates $x_6$ and $y_6$, of apertures 1070, 1072, 1074, 1076, 1078, 1080, 1082, and 1084 within primary collimator element 1004 as being proportional by the second factor to the virtual positions of virtual points of virtual collimator element 926 (FIG. 6). For example, processor 190 multiplies the virtual co-ordinates $x_{v6}$ and $y_{v6}$ of virtual point 964 (FIG. 6) with the second factor to generate the co-ordinates $x_6$ and $y_6$ of aperture 1074 of primary collimator element 1004. As another example, processor 190 multiplies the co-ordinates $x_{v7}$ and $y_{v7}$ of virtual point 966 (FIG. 6) with the second factor to generate a plurality of co-ordinates $x_7$ and $y_7$ of aperture 1076 of primary collimator element 1004.

Slot 1026 has a length in the z-direction greater than a length of primary collimator element 1004 in the z-direction. For example, slot 1026 extends, within holder 1010, from a point 1086 to a point 1088, along the z-direction and primary collimator element 1004 extends from a point 1090 to point 1088, along the z-direction. A distance, in the z-direction, between points 1088 and 1090 is less than a distance, in the z-direction, between points 1086 and 1088. The user slides, in the z-direction, primary collimator element 1004 from a side 1092 of holder 1010 into slot 1026 and from a side 1094 of holder 1016 into slot 1032 to locate primary collimator element 1004 within slots 1026 and 1032.

Figure 10:
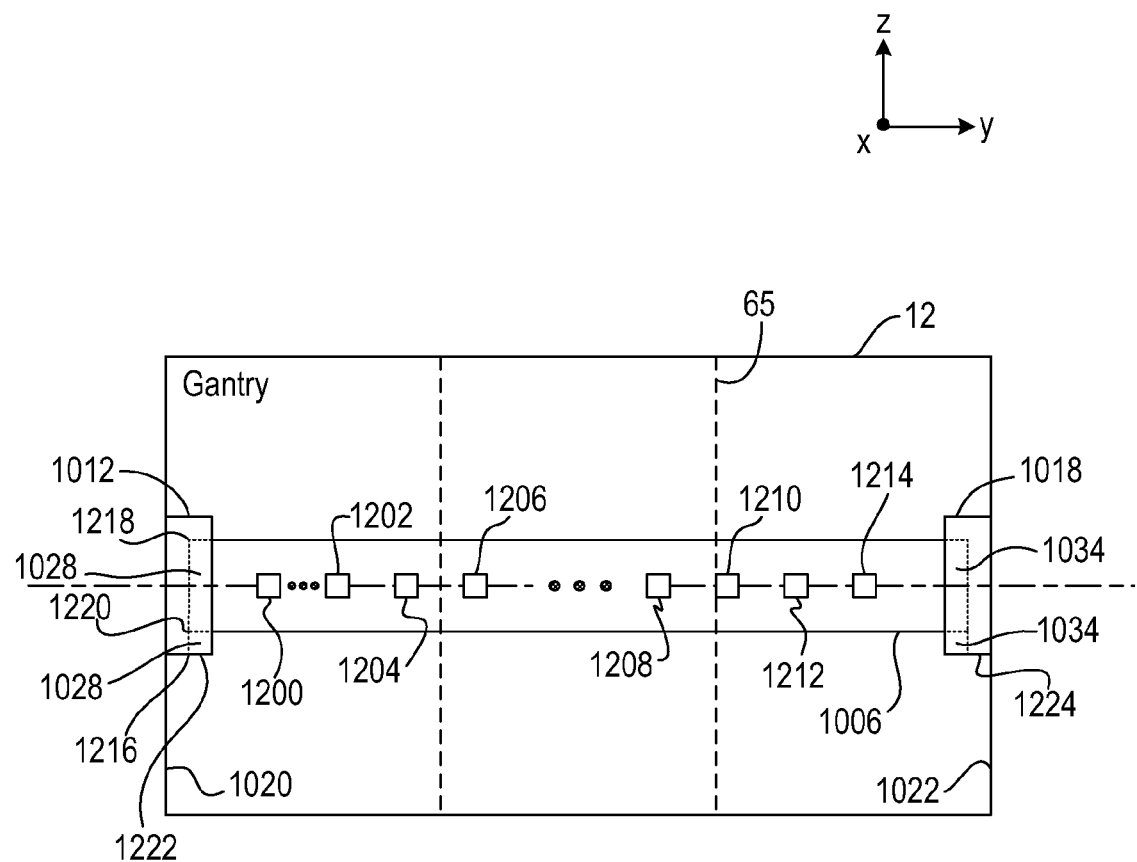
FIG. 10 is yet another top view of an embodiment of the gantry.

FIG. 10 is a top view of an embodiment of gantry 12. Gantry 12 includes primary collimator element 1006 and holders 1012 and 1018. Primary collimator element 1006 includes a plurality of apertures 1200, 1202, 1204, 1206, 1208, 1210, 1212, and 1214. A number of apertures within primary collimator element 1006 is equal to a number of virtual points on virtual collimator element 928. Processor 190 outputs a plurality of positions, such as the co-ordinates $x_8$ and $y_8$, of apertures 1200, 1202, 1204, 1206, 1208, 1210, 1212, and 1214 within primary collimator element 1006 as being proportional by the second factor to the virtual positions of virtual points of virtual collimator element 928. For example, processor 190 multiplies the virtual co-ordinates $x_{v8}$ and $y_{v8}$ of virtual point 956 with the second factor to generate the co-ordinates $x_8$ and $y_8$ of aperture 1202 of primary collimator element 1006. As another example, processor 190 multiplies the co-ordinates $x_{v9}$ and $y_{v9}$ of virtual point 958 with the second factor to generate a plurality of co-ordinates $x_9$ and $y_9$ of aperture 1204 of primary collimator element 1006.

Slot 1028 has a length in the z-direction greater than a length of primary collimator element 1006 in the z-direction. For example, slot 1028 extends, within holder 1012, from a point 1216 to a point 1218, along the z-direction and primary collimator element 1006 extends from a point 1220 to point 1218, along the z-direction. A distance, in the z-direction, between points 1218 and 1220 is less than a distance, in the z-direction, between points 1216 and 1218. The user slides, in the z-direction, primary collimator element 1006 from a side 1222 of holder 1012 into slot 1028 and a side 1224 of holder 1018 into slot 1034 to locate primary collimator element 1006 within slots 1028 and 1034.

The user creates apertures 1040, 1042, 1044, 1046, 1048, 1050, 1052, 1054, 1070, 1072, 1074, 1076, 1078, 1080, 1082, 1084, 1200, 1202, 1204, 1206, 1208, 1210, 1212, and 1214 (FIGS. 8-10) by applying a process, such as a molding process. For example, the user creates apertures 1040, 1042, 1044, 1046, 1048, 1050, 1052, and 1054 of primary collimator element 1002 by using a molding machine having a plurality of peaks of a shape of any of apertures 1040, 1042, 1044, 1046, 1048, 1050, 1052, and 1054, filling a metal, such as tungsten or molybdenum, within the molding machine, and cooling the metal to create apertures 1040, 1042, 1044, 1046, 1048, 1050, 1052, and 1054. As an example, each aperture 1040, 1042, 1044, 1046, 1048, 1050, 1052, 1054, 1070, 1072, 1074, 1076, 1078, 1080, 1082, 1084, 1200, 1202, 1204, 1206, 1208, 1210, 1212, and 1214 (FIGS. 8-10) has a width ranging from and including 0.5 mm to 1.5 mm in the y-direction, a depth ranging from and including 0.1 mm to 0.5 mm in the z-direction, and a thickness ranging from and including 2.5 mm to 5.5 mm in the x-direction. A thickness of each aperture in the x-direction is the same as a thickness, in the x-direction, of a primary collimator element that includes the aperture. For example, a thickness of aperture 1040 in the x-direction is the same as a thickness of primary collimator element 1002 in the x-direction. The user creates apertures 1040, 1042, 1044, 1046, 1048, 1050, 1052, 1054, 1070, 1072, 1074, 1076, 1078, 1080, 1082, 1084, 1200, 1202, 1204, 1206, 1208, 1210, 1212, and 1214 as having the same location, along the z-axis, as that of x-ray sources 60, 62, 64, 66, 68, 70, 72, and 74 (FIG. 1) along the z-axis.

When x-ray beam 67 (FIG. 1) passes through primary collimator 14, primary collimator 14 collimates x-ray beam 67 to generate primary beams 83 and 84 (FIG. 1) from two apertures 1046 and 1048 (FIG. 8), respectively. Alternatively or in addition, when x-ray beam 67 (FIG. 1) passes through primary collimator 14, primary collimator 14 collimates x-ray beam 67 to generate primary beams 83 and 84 (FIG. 1) from two apertures 1076 and 1078 (FIG. 9), respectively. Moreover, alternatively or in addition, when x-ray beam 67 (FIG. 1) passes through primary collimator 14, primary collimator 14 collimates x-ray beam 67 to generate primary beams 83 and 84 (FIG. 1) from two apertures 1206 and 1208, respectively. Each aperture outputs a primary beam. For example, aperture 1072 (FIG. 9) outputs a primary beam. As another example, aperture 1200 outputs a primary beam.

It is noted that an additional primary collimator element (not shown) is included within primary collimator 14 and coincides with points corresponding to a plurality of virtual points other than virtual points at which at least two beams from virtual x-ray sources 902, 904, 906, 908, 910, 912, 914, 916, 918, 920, and 922 intersect. The additional primary collimator element is parallel to any one of primary collimator elements 1002, 1004, and 1006 and includes a plurality of apertures to allow x-rays from x-ray sources 60, 62, 64, 66, 68, 70, 72, and 74 to reach any of primary collimator elements 1002, 1004, and 1006. In an alternative embodiment, primary collimator 14 does not include the additional primary collimator element.

Figure 11:
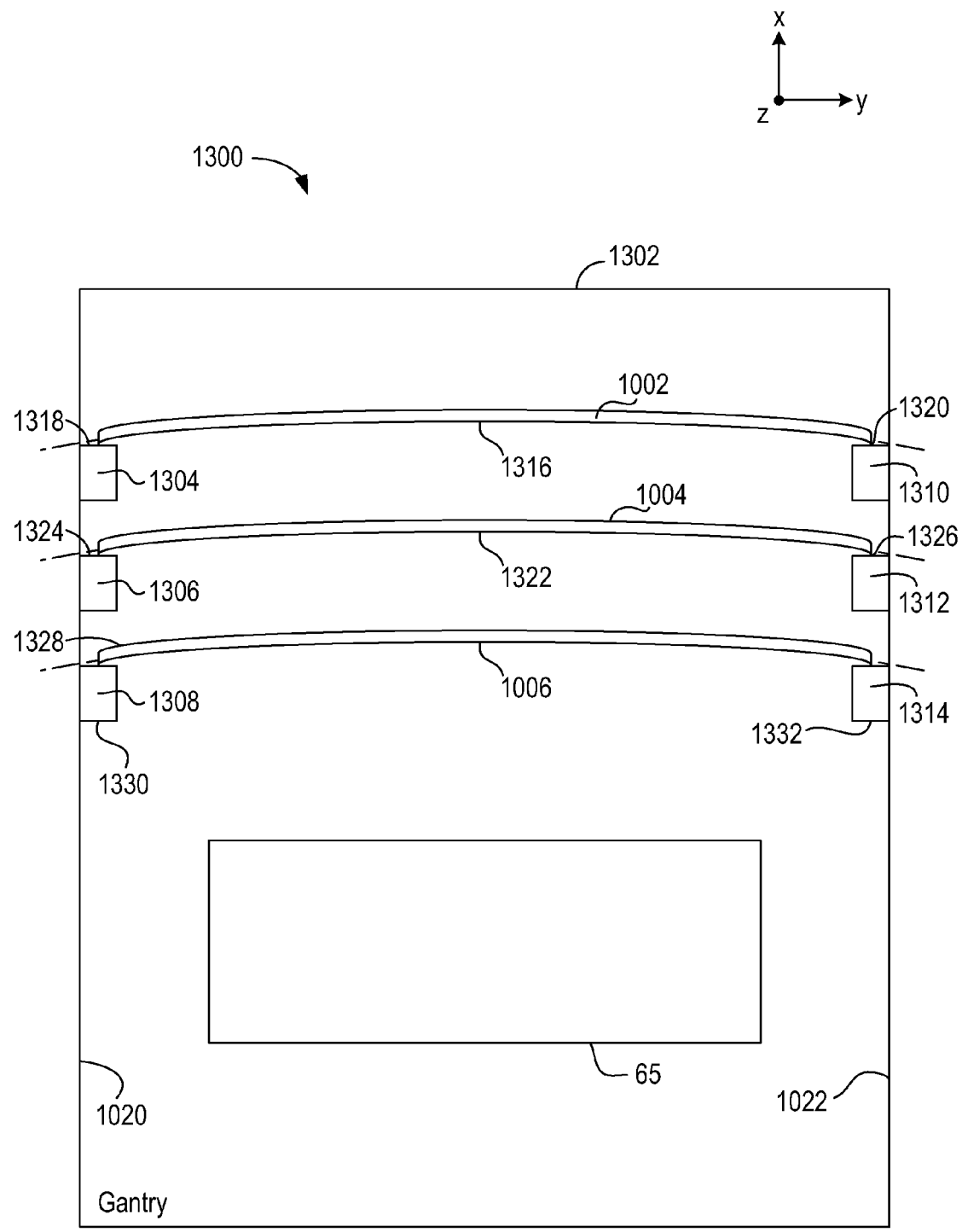
FIG. 11 is a diagram of an alternative embodiment of a gantry.

FIG. 11 is a diagram of an alternative embodiment of a gantry 1302. Gantry 1302 is an example of gantries 602 (FIG. 4) and 702 (FIG. 5). Gantry 1302 includes opening 65, a plurality of holders 1304, 1306, 1308, 1310, 1312, and 1314, and primary collimator elements 1002, 1004, and 1006. The user fabricates holders 1304, 1306, 1308, 1310, 1312, and 1314 from a metal, such as steel or aluminum. For example, the user fabricates holders 1304, 1306, 1308, 1310, 1312, and 1314 by using a molding machine including molds of a shape of any of holders 1304, 1306, 1308, 1310, 1312, and 1314, filling the molding machine with a liquid metal, such as steel, and cooling the liquid metal. The user attaches a primary collimator element to a plurality of top surfaces of holders by a process, such as spot welding or gluing, or alternatively by using screws. For example, the user attaches primary collimator element 1002 with holder 1304 by gluing a bottom surface 1316 of primary collimator element 1002 to a top surface 1318 of holder 1304 and gluing bottom surface 1316 of primary collimator element 1002 to a top surface 1320 of holder 1310. As another example, the user attaches primary collimator element 1004 with holder 1306 by spot welding a bottom surface 1322 of primary collimator element 1004 with a top surface 1324 of holder 1306 and spot welding bottom surface of primary collimator element 1004 with a top surface 1326 of holder 1312. Holders 1304, 1306, 1308, 1310, 1312, and 1314 do not include slots. Alternatively, the user attaches a top surface of a primary collimator element with a plurality of bottom surfaces of holders. For example, the user attaches a top surface 1328 of primary collimator element 1006 with a bottom surface 1330 of holder 1308 and a bottom surface 1332 of holder 1314.

Figure 12:
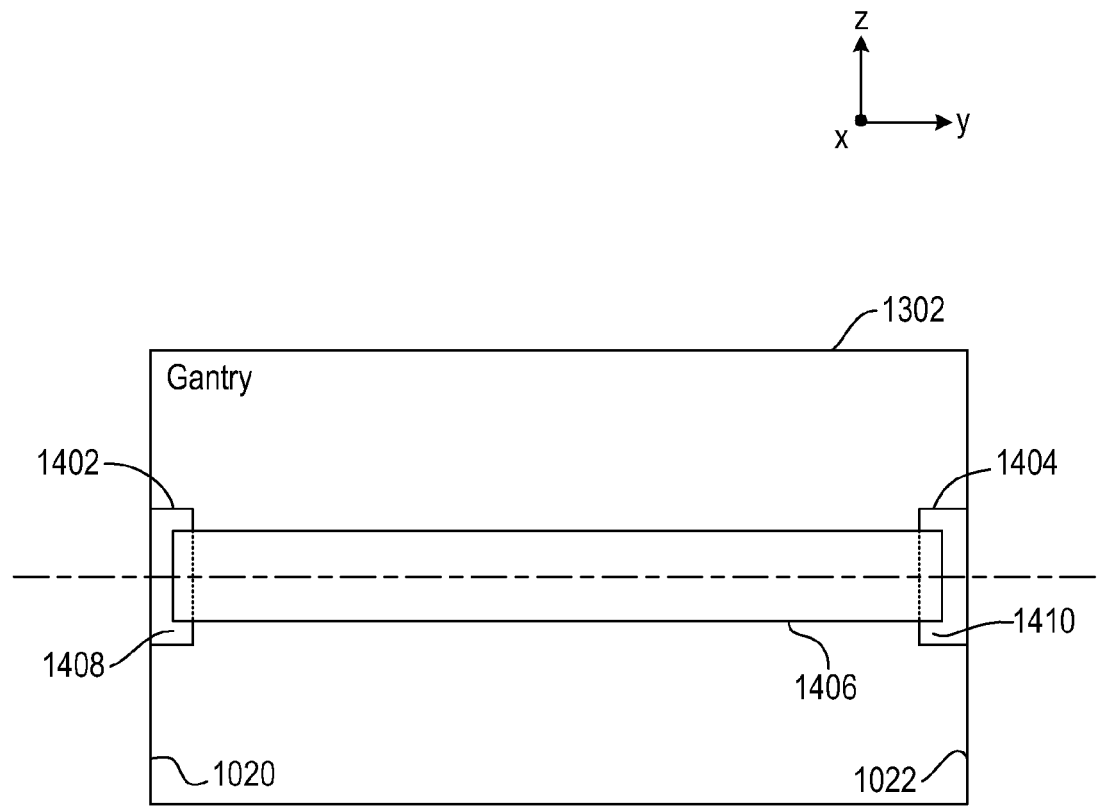
FIG. 12 is a top view of the gantry of FIG. 11.

FIG. 12 is a top view of an embodiment of gantry 1302. Gantry 1302 includes a plurality of holders 1402 and 1404, and a primary collimator element 1406. Primary collimator element 1406 is an example of any of primary collimator elements 1002, 1004, and 1006 (FIG. 11). Holders 1402 and 1404 are examples of holders 1304 and 1310 (FIG. 11), respectively, if primary collimator element 1406 is an example of primary collimator element 1002. Holders 1402 and 1404 are examples of holders 1306 and 1312 (FIG. 11), respectively, if primary collimator element 1406 is an example of primary collimator element 1004. Holders 1402 and 1404 are examples of holders 1308 and 1314 (FIG. 11), respectively, if primary collimator element 1406 is an example of primary collimator element 1006. Primary collimator element 1406 is attached to a top surface 1408 of holder and to a top surface 1410 of holder.

Technical effects of the herein described systems and methods for generating an improved diffraction profile include increasing a single-to-noise ratio detected by providing at least two scatter detectors, such as scatter detectors 16 and 18, to detect scattered radiation. Other technical effects include examining by at least two scatter detectors, such as scatter detectors 16 and 18, of container 79 that is larger than a container (not shown) examined by a single scatter detector. Yet other technical effect includes an improved coverage of container 79 with primary x-rays. Still other technical effects include providing an improved diffraction profile by measuring energy at points 94 and 95. Yet other technical effects include a reduction in power consumed by x-ray sources 60, 62, 64, 66, 68, 70, 72, and 74. The reduction in power is achieved by using a plurality of scatter detectors, such as scatter detectors 16 and 18, to detect scattered radiation. The power consumed by x-ray sources 60, 62, 64, 66, 68, 70, 72, and 74 to generate a diffraction profile having a certain quality is reduced compared to a power consumed by a plurality of x-ray sources to provide x-rays to a single scatter detector that is used to generate the diffraction profile of the same quality. For example, a plurality of x-ray sources consume a high amount, such as 90 kilowatts (kW), of power to acquire a number of scattered x-ray photons detected by a single scatter detector in a restricted scan time to generate a diffraction profile of the scattered x-ray photons. The high amount of power is higher than a low amount, such as at most half of the high amount, of power consumed by x-ray sources 60, 62, 64, 66, 68, 70, 72, and 74 to acquire the number of scattered x-ray photons detected by at least two scatter detectors, such as scatter detectors 16 and 18, in the restricted scan time.

The scatter angle 98 is larger than, such as at least twice compared to, scatter angle 96. Energy of scattered x-ray photons scattered from point 85 onto scatter detector 18 is at least twice that of energy of scattered x-ray photons scattered from point 85 onto detector 16 at the same momentum transfer $x_A$. As a result, most of scattered x-ray photons from point 85 onto scatter detector 16 are absorbed by container 79. Moreover, energy of scattered x-ray photons scattered from point 85 onto scatter detector 18 is at least twice that of energy of scattered x-ray photons scattered from point 86 onto scatter detector 18 at the same momentum transfer $x_A$. As a result, most of scattered x-ray photons from point 86 onto scatter detector 18 are absorbed by container 79. Furthermore, energy of scattered x-ray photons scattered from point 85 onto scatter detector 708 is at least twice that of energy of scattered x-ray photons scattered from point 85 onto detector 710 at the same momentum transfer $x_B$. As a result, most of scattered x-ray photons from point 85 onto scatter detector 710 are absorbed by container 79. Moreover, energy of scattered x-ray photons scattered from point 85 onto scatter detector 708 is at least twice that of energy of scattered x-ray photons scattered from point 86 onto detector 708 at the same momentum transfer $x_B$. As a result, most of scattered x-ray photons from point 86 onto scatter detector 708 are absorbed by container 79. Energies, such as ranging from and including 30 kiloelectron volts (keV) to 200 keV, of scattered x-ray photons at scatter angle 98 detected by scatter detector 16 is lower than energies of scattered x-ray photons at scatter angle 96 detected by scatter detector 18. As a result, most of scattered x-ray photons within scattered radiation 89 are attenuated by container 79.

Moreover, scattered x-ray photons within scattered radiation 89 can be absorbed by a filter, such as a metal or a copper filter, placed between support 80 and secondary collimator 76. Absorption of scattered x-ray photons within scattered radiation 89 by container 79 and/or the filter prevents an overload and a dead time of scatter detector 16. Moreover, absorption of scattered x-ray photons within scattered radiation 89 by container 79 and/or the filter prevents an interference of the scattered x-ray photons with scattered radiation 88.

While the invention has been described in terms of various specific embodiments, those skilled in the art will recognize that the invention can be practiced with modification within the spirit and scope of the claims.

What is claimed is:

1. A system for generating a diffraction profile of an object, said system comprising:
    at least one x-ray source configured to generate x-rays;
    a primary collimator configured to divide the generated x-rays into a first x-ray beam directed to a first focus point within an object space and a second x-ray beam directed to a second focus point within the object space; and
    a first scatter detector configured to:
        detect a first set of scattered radiation generated upon intersection of the first x-ray beam with the object at a first point on said first scatter detector; and
        detect a second set of scattered radiation generated upon intersection of the second x-ray beam with the object at the first point on said first scatter detector.

2. A system in accordance with claim 1, further comprising a second scatter detector separated by a gap from said first scatter detector, said second scatter detector configured to:
    detect a third set of scattered radiation generated upon intersection of the first x-ray beam with the object; and
    detect a fourth set of scattered radiation generated upon intersection of the second x-ray beam with the object, the third set of scattered radiation and the fourth set of scattered radiation detected at a second point on said second scatter detector.

3. A system in accordance with claim 2, wherein an angle of scatter of the first set of scattered radiation detected by said first scatter detector is equal to an angle of scatter of the third set of scattered radiation detected by said second scatter detector.

4. A system in accordance with claim 1, wherein an angle of scatter of the first set of scattered radiation detected by said first scatter detector is at most one-half of an angle of scatter of the second set of scattered radiation detected by said first scatter detector.

5. A system in accordance with claim 2, further comprising:
    a third scatter detector configured to detect a fifth set of scattered radiation generated upon intersection of the first x-ray beam with the object; and
    a fourth scatter detector configured to detect a sixth set of scattered radiation generated upon intersection of the second x-ray beam with the object.

6. A system in accordance with claim 1, further comprising a transmission detector configured to detect the first x-ray beam and the second x-ray beam.

7. A system in accordance with claim 5, further comprising:
    a transmission detector configured to detect the first x-ray beam and the second x-ray beam; and
    a gantry, wherein said transmission detector, said first scatter detector, said second scatter detector, said third scatter detector, and said fourth scatter detector are located within said gantry.

8. A system for generating a diffraction profile of an object, said system comprising:
    at least one x-ray source configured to generate x-rays;
    a primary collimator configured to divide the generated x-rays into a first x-ray beam directed to a first focus point within an object space and a second x-ray beam directed to a second focus point within the object space;
    a first scatter detector configured to:
        detect a first set of scattered radiation generated upon intersection of the first x-ray beam with the object at a first point on said first scatter detector; and
        detect a second set of scattered radiation generated upon intersection of the second x-ray beam with the object at the first point on said first scatter detector; and
    a processor coupled to said first scatter detector and configured to generate a portion of a diffraction profile of the object from the first set of scattered radiation and the second set of scattered radiation detected by said first scatter detector.

9. A system in accordance with claim 8, further comprising a second scatter detector separated by a gap from said first scatter detector, said second scatter detector configured to:
    detect a third set of scattered radiation generated upon intersection of the first x-ray beam with the object; and
    detect a fourth set of scattered radiation generated upon intersection of the second x-ray beam with the object, the third set of scattered radiation and the fourth set of scattered radiation detected at a second point on said second scatter detector.

10. A system in accordance with claim 9, wherein an angle of scatter of the first set of scattered radiation detected by said first scatter detector is equal to an angle of scatter of the third set of scattered radiation detected by said second scatter detector.

11. A system in accordance with claim 9, further comprising:
    a third scatter detector configured to detect a fifth set of scattered radiation generated upon intersection of the first x-ray beam with the object; and
    a fourth scatter detector configured to detect a sixth set of scattered radiation generated upon intersection of the second x-ray beam with the object.

12. A system in accordance with claim 11, further comprising a transmission detector configured to detect the first x-ray beam and the second x-ray beam, wherein said first and second scatter detectors are placed on a first side of said transmission detector, the first side is opposite to a second side of said transmission detector, and said third and fourth scatter detectors are placed on the second side.

13. A system in accordance with claim 9, further comprising:
    a transmission detector configured to detect the first x-ray beam and the second x-ray beam; and
    a gantry, wherein said transmission detector, said first scatter detector, and said second scatter detector are located within said gantry.

14. A system in accordance with claim 8, wherein an angle of scatter of the first set of scattered radiation detected by said first scatter detector is at most one-half of an angle of scatter of the second set of scattered radiation detected by said first scatter detector.

15. A method for generating a diffraction profile of an object, said method comprising:
    generating x-rays by activating at least one x-ray source;
    dividing the generated x-rays, using a primary collimator, into a first x-ray beam directed to a first focus point within an object space and a second x-ray beam directed to a second focus point within the object space;
    detecting a first set of scattered radiation generated upon intersection of the first x-ray beam with the object at a first point on a first scatter detector; and
    detecting a second set of scattered radiation generated upon intersection of the second x-ray beam with the object at the first point on the first scatter detector.

16. A method in accordance with claim 15, further comprising:

collimating the first set of scattered radiation for detection by the first scatter detector, the first set of scattered radiation collimated to impinge on the first scatter detector at the first point; and collimating the second set of scattered radiation for detection by the first scatter detector, the second set of scattered radiation collimated to impinge on the first scatter detector at the first point.

17. A method in accordance with claim 15, further comprising:

detecting, by a second scatter detector, a third set of scattered radiation generated upon intersection of the first x-ray beam with the object;

detecting, by the second scatter detector, a fourth set of scattered radiation generated upon intersection of the second x-ray beam with the object, the third set of scattered radiation and the fourth set of scattered radiation detected at a second point on the second scatter detector;

collimating the third set of scattered radiation for detection by the second scatter detector, the third set of scattered radiation collimated to impinge on the second scatter detector at the second point; and collimating the fourth set of scattered radiation for detection by the second scatter detector, the fourth set of scattered radiation collimated to impinge on the second scatter detector at the second point.

18. A method in accordance with claim 17, further comprising:

detecting, by a transmission detector, the first x-ray beam and the second x-ray beam;

detecting, by a third scatter detector, a fifth set of scattered radiation generated upon intersection of the first x-ray beam with the object; and detecting, by a fourth scatter detector, a sixth set of scattered radiation generated upon intersection of the second x-ray beam with the object, wherein the first and second scatter detectors are placed on a first side of the transmission detector, the first side is opposite to a second side of the transmission detector, and the third and fourth scatter detectors are placed on the second side.

19. A method in accordance with claim 17, further comprising:

detecting, by a third scatter detector, a fifth set of scattered radiation generated upon intersection of the first x-ray beam with the object; and detecting, by a fourth scatter detector, a sixth set of scattered radiation generated upon intersection of the second x-ray beam with the object.

20. A method in accordance with claim 19, further comprising:

collimating the fifth set of scattered radiation for detection by the third scatter detector, the fifth set of scattered radiation collimated to impinge on the third scatter detector at a third point; and collimating the sixth set of scattered radiation for detection by the fourth scatter detector, the sixth set of scattered radiation collimated to impinge on the fourth scatter detector at a fourth point.

* * * * *